United States Patent
Nagai et al.

(10) Patent No.: US 7,956,142 B2
(45) Date of Patent: Jun. 7, 2011

(54) POLYMERIZABLE SULFONIC ACID ONIUM SALT AND RESIN

(75) Inventors: Tomoki Nagai, Tokyo (JP); Takuma Ebata, Tokyo (JP); Makoto Shimizu, Tokyo (JP); Jonathan Joachim Jodry, Kawagoe (JP); Satoru Narizuka, Kawagoe (JP); Masaki Fujiwara, Kawagoe (JP)

(73) Assignees: JSR Corporation, Tokyo (JP); Central Glass Co., Ltd., Yamaguchi (JP)

( * ) Notice: Subject to any disclaimer, the term of this patent is extended or adjusted under 35 U.S.C. 154(b) by 0 days.

(21) Appl. No.: 12/514,168

(22) PCT Filed: Nov. 9, 2007

(86) PCT No.: PCT/JP2007/071849
§ 371 (c)(1),
(2), (4) Date: May 8, 2009

(87) PCT Pub. No.: WO2008/056795
PCT Pub. Date: May 15, 2008

(65) Prior Publication Data
US 2010/0063232 A1    Mar. 11, 2010

(30) Foreign Application Priority Data
Nov. 10, 2006   (JP) .................................. 2006-305842

(51) Int. Cl.
*C08F 128/02*   (2006.01)
(52) U.S. Cl. ...................................................... 526/287
(58) Field of Classification Search ................... 526/287
See application file for complete search history.

(56) References Cited

U.S. PATENT DOCUMENTS

| | | |
|---|---|---|
| 4,491,628 A | 1/1985 | Ito et al. |
| 2006/0147836 A1 | 7/2006 | Hatakeyama et al. |
| 2009/0069521 A1* | 3/2009 | Nagai et al. ................... 526/243 |

FOREIGN PATENT DOCUMENTS

| | | |
|---|---|---|
| CA | 2049772 A | 2/1992 |
| JP | 2-27660 B | 3/1984 |
| JP | 4-230645 A | 8/1992 |
| JP | 11-338146 A | 12/1999 |
| JP | 2004-322378 A | 11/2004 |
| JP | 2005-84365 A | 3/2005 |
| JP | 2006-215526 A | 8/2006 |
| JP | 2008-297234 A | 12/2008 |
| JP | 2009-007327 A | 1/2009 |
| WO | 2008/099869 A1 | 8/2008 |

OTHER PUBLICATIONS

Organic Letters, 2001, vol. 3, No. 17, p. 2769-2771, Pan et al.*
Federal Register Oct. 18, 2000 (vol. 65, No. 202), "Perfluorooctyl Sulfonates; Proposed Significant New Use Rule".
Nakamura et al., "Resist Surface Roughness Calculated using Theoretical Percolation Model", Journal of Photopolymer Science and Technology, vol. 11, No. 4, 1998, pp. 571-576.
Shiobara et al., "Resist Edge Roughness with Reducing Pattern Size", SPIE vol. 3333, pp. 313-323.
Palmateer et al., "Line Edge Roughness in sub-0.18-µm Resist Patterns", SPIE vol. 3333, pp. 634-642.
Namatsu et al., "Three-dimensional siloxane resist for the formation of nanopatterns with minimum linewidth fluctuations", J. Vac. Sci. Technol. B, vol. 16, No. 1, Jan./Feb. 1998, pp. 69-76.

* cited by examiner

*Primary Examiner* — Ling-Siu Choi
*Assistant Examiner* — Sonya Wright
(74) *Attorney, Agent, or Firm* — Ditthavong Mori & Steiner, P.C.

(57) ABSTRACT

A resin that includes a repeating unit shown by the following formula (10) has an excellent performance as a radiation sensitive acid generator, and exhibits only a small adverse effect on the environment and a human body.

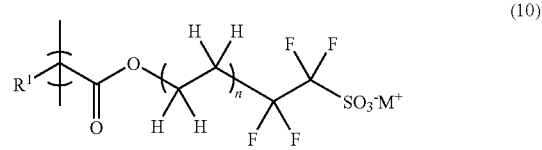

wherein $R^1$ represents a hydrogen atom or the like, $M^+$ represents a specific cation, and n is an integer from 1 to 5.

4 Claims, No Drawings

US 7,956,142 B2

POLYMERIZABLE SULFONIC ACID ONIUM SALT AND RESIN

TECHNICAL FIELD

The present invention relates to (1) a polymerizable onium sulfonate for producing a resin which functions as an acid generator, (2) a process for producing the polymerizable onium sulfonate, and (3) a resin which functions as an acid generator.

BACKGROUND ART

A lithography process using near ultraviolet rays such as an I-ray as radiation has generally been used in the manufacture of integrated circuit devices. Microfabrication in a sub-quarter micron order is said to be achieved with extreme difficulty if the near ultraviolet rays are used. Therefore, achieving a higher degree of integration by using near ultraviolet rays has been difficult. For this reason, a lithography process which can achieve microfabrication with a higher degree (microfabrication of 0.20 μm or less) has been demanded.

As a means for achieving such microfabrication in the order of 0.20 μm or less, a lithography process utilizing a radiation with a wavelength shorter than that of the near ultraviolet rays is studied. As examples of radiation having such a short wavelength, deep ultraviolet rays represented by a bright line spectrum of a mercury lamp and an excimer laser, X-rays, and electron beams can be given. Among these, a KrF excimer laser (wavelength: 248 nm), an ArF excimer laser (wavelength: 193 nm), an $F_2$ excimer laser (wavelength: 157 nm), EUV (wavelength: 13 nm, etc.), and electron beams are attracting attention.

Along with the reduction of the radiation wavelength used in the lithography processes, a number of radiation-sensitive resin compositions suitable for use with short wavelength radiation have been proposed. As such a radiation-sensitive resin composition, a composition utilizing a chemical amplification effect between a component having an acid-dissociable functional group and a radiation sensitive acid generator which generates an acid upon exposure to radiation (hereinafter referred to as "exposure") have been proposed. Such a composition is hereinafter referred to as a chemically-amplified radiation sensitive composition.

As a specific example of the chemically-amplified radiation sensitive composition, a composition containing a polymer having a t-butyl ester group of a carboxylic acid or a t-butyl carbonate group of phenol and a radiation sensitive acid generator has been proposed (see Patent Document 1). This composition forms an acidic group consisting of a carboxyl group or a phenolic hydroxyl group by dissociating the t-butyl ester group or the t-butyl carbonate group in the polymer by the action of an acid which is produced by exposure to radiation. Therefore, the portion exposed to radiation (exposed area) on the resist film formed from the composition becomes easily soluble in an alkaline developer. For that reason, a desired resist pattern can be formed on a resist film by developing using an alkaline developer.

The radiation sensitive acid generator contained in the chemically-amplified radiation sensitive composition is required to have excellent transparency to radiation and to exhibit a high quantum yield when generating an acid. The acid generated by the radiation sensitive acid generator must be sufficiently strong, must have a sufficiently high boiling point, and must have an appropriate diffusion length (hereinafter referred to from time to time as "diffusion length") in a resist film.

In order to have strong acidity and a high boiling point, and to exhibit an appropriate diffusion length, the structure of the anion moiety of an ionic radiation sensitive acid generator is important. In the case of the nonionic radiation sensitive acid generator having a sulfonyl structure or a sulfonate structure, the structure of the sulfonyl moiety is important.

For example, in the case of a radiation sensitive acid generator having a trifluoromethanesulfonyl structure, the generated acid has sufficiently high acidity and can produce a composition having sufficiently high resolution performance as a photoresist. However, such a composition has a drawback of high mask dependency as a photoresist due to the low boiling point and high diffusion length of the acid which is undesirable as a resist. For example, in the case of a radiation sensitive acid generator having a sulfonyl structure containing a large organic group such as a 10-camphor sulfonyl structure, the mask dependency is small due to the sufficiently high boiling point and sufficiently short diffusion length of the acid produced which is desirable as a resist. However, the composition exhibits only insufficient resolution performance as a photoresist due to insufficient acidity.

A radiation sensitive acid generator having a perfluoroalkylsulfonyl structure such as perfluoro-n-octanesulfonate (PFOS) has attracted an attention in recent years due to the capability of generating an acid having sufficiently high acidity, sufficiently high boiling point, and an almost appropriate diffusion length.

However, the radiation sensitive acid generators having a perfluoroalkylsulfonyl structure such as PFOS are said to cause environmental problems due to low combustibility. In addition, these compounds are suspected to accumulate in the human body. According to a report issued by the United States Environmental Protection Agency, a regulation to rule out the use of these compounds has been proposed (see Non-patent Document 1).

When more accurate control of a line width is necessary, such as a case in which the designed dimension of a device is sub-half-micron or less, a chemically-amplified resist is required to have not only excellent resolution performance, but also excellent film surface smoothness after resist pattern formation. A chemically-amplified resist having poor film surface smoothness transfers irregularities of the film surface (hereinafter referred to from time to time as "nano-edge roughness") onto the substrate when transferring the resist pattern by etching or the like. As a result, such a chemically-amplified resist impairs the pattern dimensional accuracy. Such a chemically-amplified resist is thus reported to impair electrical properties of ultimately produced devices (see, for example, Non-patent Documents 2 to 5).

Patent Document 1: JP-B-2-27660
Non-patent Document 1: Perfluorooctyl Sulfonates; Proposed Significant New Use Rule
Non-patent Document 2: J. Photopolym. Sci. Tech., p. 571 (1998)
Non-patent Document 3: Proc. SPIE, Vol. 3333, p. 313
Non-patent Document 4: Proc. SPIE, Vol. 3333, p. 634
Non-patent Document 5: J. Vac. Sci. Technol. B16 (1), p. 69 (1998)

DISCLOSURE OF THE INVENTION

For the above-mentioned reasons, development of a radiation sensitive acid generator which does not have the defects of radiation sensitive acid generators having a perfluoroalkylsulfonyl structure such as PFOS, exhibits excellent resolution performance, and can be used in a composition capable of forming a chemically-amplified resist exhibiting only small nano-edge roughness is urgently demanded.

The present invention has been made in view of the above problems of the related art, and has an object of providing an onium sulfonate which is polymerizable, can produce an acid with sufficiently high acidity, exhibits good combustibility, and does not accumulate in the human body.

Another object of the present invention is to provide a simple process for producing the polymerizable onium sulfonate in high yield.

Still another object of the present invention is to provide a resin exhibiting excellent transparency to deep ultraviolet rays and electron beams represented by activated radiation, particularly a KrF excimer laser, an ArF excimer laser, an $F_2$ excimer laser, or EUV, excellent functions as a radiation sensitive acid generator or a thermal acid generator responsive to the activated radiations, good combustibility, and small accumulability in the human body.

The inventors of the present invention have conducted extensive studies in order to achieve the above objects. As a result, the inventors have found that the above objects can be achieved by a polymerizable onium sulfonate having a specific structure and a resin containing a repeating unit derived from the polymerizable onium sulfonate. This finding has led to the completion of the present invention.

According to the present invention, the following polymerizable onium sulfonate, process for producing the polymerizable onium sulfonate, and resin are provided.

[1] A polymerizable onium sulfonate shown by the following formula (1),

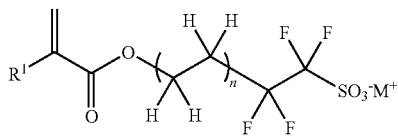

(1)

wherein $R^1$ represents a hydrogen atom, a fluorine atom, or an alkyl group having 1 to 3 carbon atoms, in which some or all of the hydrogen atoms may be substituted by a fluorine atom, $M^+$ represents a sulfonium cation shown by the following formula (2) or an iodonium cation shown by the following formula (3), and n represents an integer from 1 to 5,

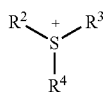

(2)

wherein $R^2$, $R^3$, and $R^4$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or two or more of $R^2$, $R^3$, and $R^4$ may bond to form a ring together with the sulfur atom in the formula (2),

wherein $R^5$ and $R^6$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or $R^5$ and $R^6$ may bond to form a ring together with the iodine atom in the formula (3).

[2] The polymerizable onium sulfonate according to [1], the polymerizable onium sulfonate being a compound shown by the following formula (I-1),

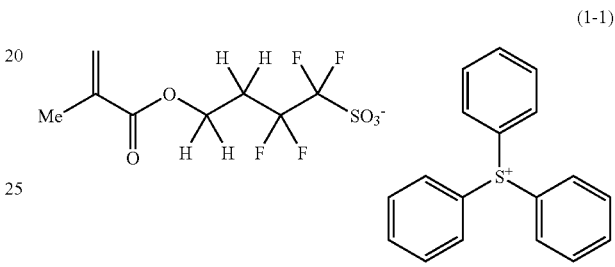

(I-1)

[3] A process for producing a polymerizable onium sulfonate comprising a first step of sulfinating 4-bromo-3,3,4,4-tetrafluorobutan-1-ol using a sulfinating agent to obtain a metal sulfinate shown by the following formula (4), a second step of oxidizing the metal sulfinate using an oxidizer to obtain a metal sulfonate shown by the following formula (5), a third step of reacting the metal sulfonate with a monovalent onium salt shown by the following formula (6) to obtain an onium sulfonate shown by the following formula (7), and a fourth step of reacting the onium sulfonate with an alkyl acrylic acid halide shown by the following formula (8) or an alkyl acrylic acid anhydride shown by the following formula (9) to obtain a polymerizable onium sulfonate shown by the following formula (1-a),

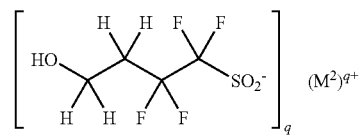

(4)

wherein $(M^2)^{q+}$ shows a counter cation that is a metal ion and q is an arbitrary integer,

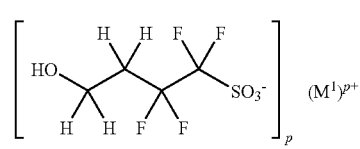

(5)

wherein $(M^1)^{p+}$ shows a counter cation that is a metal ion and p is an arbitrary integer,

$$M^+X^-$$ (6)

wherein M⁺ shows a sulfonium cation shown by the following formula (2) or an iodonium cation shown by the following formula (3) and X⁻ shows a monovalent anion, $$R^2\underset{R^4}{\overset{+}{\underset{|}{S}}}R^3 \quad (2)$$

wherein $R^2$, $R^3$, and $R^4$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or two or more of $R^2$, $R^3$, and $R^4$ may bond to form a ring together with the sulfur atom in the formula (2), $$R^5\text{—}\overset{+}{I}\text{—}R^6 \quad (3)$$

wherein $R^5$ and $R^6$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or $R^5$ and $R^6$ may bond to form a ring together with the iodine atom in the formula (3), (7)

HO—CH(H)—CF(F)—CH(H)—CF(F)—SO₃⁻ M⁺ wherein M⁺ is the same as the M⁺ in the formula (6), (8)

$R^1$—C(=O)—X⁴ (with vinyl group)

wherein $R^1$ represents a hydrogen atom, a fluorine atom, or an alkyl group having 1 to 3 carbon atoms, in which some or all of the hydrogen atoms may be substituted by a fluorine atom, $X^4$ represents a fluorine atom, a chlorine atom, a bromine atom, or an iodine atom, (9)

$R^1$—C(=O)—CH₂—C(=O)—$R^1$ (with vinyl groups)

wherein $R^1$ is the same as the $R^1$ in the formula (8), (1-a)

$R^1$—C(=O)—O—CH(H)—CH(H)—CF(F)—CF(F)—SO₃⁻ M⁺ wherein $R^1$ is the same as the $R^1$ in the formula (8) and M⁺ is the same as the M⁺ in the formula (6).

[4] A resin comprising a repeating unit shown by the following formula (10), (10)

$R^1$—[repeating unit with ester linkage —O—(CH₂CF₂)ₙ—SO₃⁻ M⁺]

wherein $R^1$ represents a hydrogen atom, a fluorine atom, or an alkyl group having 1 to 3 carbon atoms, in which some or all of the hydrogen atoms may be substituted by a fluorine atom, M⁺ represents a sulfonium cation shown by the following formula (2) or an iodonium cation shown by the following formula (3), and n represents an integer from 1 to 5, $$R^2\underset{R^4}{\overset{+}{\underset{|}{S}}}R^3 \quad (2)$$

wherein $R^2$, $R^3$, and $R^4$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or two or more of $R^2$, $R^3$, and $R^4$ may bond to form a ring together with the sulfur atom in the formula (2), $$R^5\text{—}\overset{+}{I}\text{—}R^6 \quad (3)$$

wherein $R^5$ and $R^6$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or $R^5$ and $R^6$ may bond to form a ring together with the iodine atom in the formula (3).

The polymerizable onium sulfonate of the present invention produces an acid with sufficiently high acidity by exposure to radiation, exhibits good combustibility and low accumulability in the human body, and is polymerizable.

The process for producing a polymerizable onium sulfonate of the present invention can produce the polymerizable onium sulfonate in high yield by a simple method.

The resin of the present invention exhibits excellent transparency to deep ultraviolet rays and electron beams represented by activated radiation, particularly a KrF excimer laser, an ArF excimer laser, an $F_2$ excimer laser, or EUV, excellent functions as a radiation sensitive acid generator or a thermal acid generator responsive to the activated radiation, good combustibility, and small accumulability in the human body.

BEST MODE FOR CARRYING OUT THE INVENTION

Preferred embodiments of the present invention are described below. Note that the present invention is not limited to the following embodiments. Various modifications and improvements may be made in the following embodiments within the scope of the present invention based on the knowledge of a person skilled in the art.

[1] Polymerizable Onium Sulfonate

The polymerizable onium sulfonate is shown by the following formula (1). Since the polymerizable onium sulfonate has a polymerizable site, a resin having an onium sulfonate structure, specifically, a resin having the repeating unit shown by the formula (10) described later, can be obtained by polymerizing the compound shown by the formula (1). Due to possession of an onium sulfonate structure, the resin obtained in this manner can function as an acid generator which generates an acid by exposure to radiation.

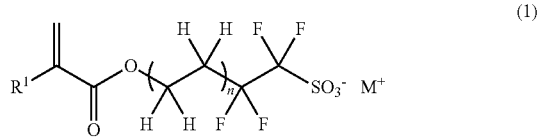

(1)

wherein $R^1$ represents a hydrogen atom, a fluorine atom, or an alkyl group having 1 to 3 carbon atoms, in which some or all of the hydrogen atoms may be substituted by a fluorine atom, $M^+$ represents a sulfonium cation shown by the following formula (2) or an iodonium cation shown by the following formula (3), and n represents an integer from 1 to 5,

(2)

wherein $R^2$, $R^3$, and $R^4$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or two or more of $R^2$, $R^3$, and $R^4$ may bond to form a ring together with the sulfur atom in the formula (2),

(3)

wherein $R^5$ and $R^6$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or $R^5$ and $R^6$ may bond to form a ring together with the iodine atom in the formula (3).

As examples of the unsubstituted linear or branched alkyl group having 1 to 30 carbon atoms represented by $R^2$, $R^3$, and $R^4$ in the formula (2), a methyl group, an ethyl group, an n-propyl group, an i-propyl group, an n-butyl group, a 1-methylpropyl group, a 2-methylpropyl group, a t-butyl group, an n-pentyl group, an i-pentyl group, a 1,1-dimethylpropyl group, a 1-methylbutyl group, a 1,1-dimethylbutyl group, a n-hexyl group, an n-heptyl group, an i-hexyl group, an n-octyl group, an i-octyl group, a 2-ethylhexyl group, an n-nonyl group, an n-decyl group, an n-undecyl group, an n-dodecyl group, a cyclopropyl group, a cyclopentyl group, a cyclohexyl group, and a 4-t-butylcyclohexyl group can be given.

As examples of the substituents for the substituted linear or branched alkyl group having 1 to 30 carbon atoms, an aryl group having 6 to 30 carbon atoms, a linear, branched, or cyclic alkenyl group having 2 to 30 atoms, and a group having 1 to 30 atoms containing a hetero atom such as a halogen atom, an oxygen atom, a nitrogen atom, a sulfur atom, a phosphorus atom, or a silicon atom can be given. These substituents may be substituted by any optional substituents, for example, by one or more of the above-mentioned substituents.

As examples of the monovalent cyclic hydrocarbon group having 3 to 30 carbon atoms, a cyclohexenyl group, a group having a norbornene skeleton, a group having a norbornane skeleton, a group having an isobornyl skeleton, a group having a tricyclodecane skeleton, a group having a tetracyclododecane skeleton, and a group having an adamantane skeleton can be given.

As the substituent for the substituted monovalent cyclic hydrocarbon group having 3 to 30 carbon atoms, the same groups as the above-mentioned substituted linear substituents having 1 to 30 carbon atoms can be given.

As examples of substituent for the substituted monovalent cyclic hydrocarbon group having 3 to 30 carbon atoms, a benzyl group, a methoxymethyl group, a methylthiomethyl group, an ethoxymethyl group, an ethylthiomethyl group, a phenoxymethyl group, a methoxycarbonylmethyl group, an ethoxycarbonylmethyl group, an acetylmethyl group, a fluoromethyl group, a trifluoromethyl group, a chloromethyl group, a trichloromethyl group, a 2-fluoropropyl group, a (trifluoroacetyl)methyl group, a (trichloroacetyl)methyl group, a (pentafluorobenzoyl)methyl group, an aminomethyl group, a (cyclohexylamino)methyl group, a (diphenylphosphino)methyl group, a (trimethylsilyl)methyl group, a 2-phenylethyl group, a 3-phenylpropyl group and a 2-aminoethyl group can be given.

As examples of the unsubstituted aryl group having 6 to 30 carbon atoms, a phenyl group, a 1-naphthyl group, a 2-naphthyl group, a 1-anthryl group, and a 1-phenanthryl group can be given.

As examples of the substituents of these aryl groups, a linear, branched, or cyclic alkyl group having 1 to 30 carbon atoms, and a group having 1 to 30 atoms containing a hetero atom such as a halogen atom, an oxygen atom, a nitrogen atom, a sulfur atom, a phosphorus atom, or a silicon atom can be given. These substituent groups may further be substituted by any optional substituents, for example, by one or more of the above-mentioned substituents.

As examples of the substituted aryl group having 6 to 30 carbon atoms, an o-tolyl group, an m-tolyl group, a p-tolyl group, a p-hydroxyphenyl group, a p-methoxyphenyl group, a mesityl group, an o-cumenyl group, a 2,3-xylyl group, a 2,4-xylyl group, a 2,5-xylyl group, a 2,6-xylyl group, a 3,4- xylyl group, a 3,5-xylyl group, a p-fluorophenyl group, a p-trifluoromethylphenyl group, a p-chlorophenyl group, a p-bromophenyl group, and a p-iodophenyl group can be given.

As examples of the unsubstituted monovalent heterocyclic monovalent organic group having 4 to 30 atoms, a furyl group, a thienyl group, a pyranyl group, a pyrrolyl group, a thianthrenyl group, a pyrazolyl group, an iso-thiazolyl group, an iso-oxazolyl group, a pyrazinyl group, a pyrimidinyl group, a pyridazinyl group, a tetrahydropyranyl group, a tetrahydrofuranyl group, a tetrahydrothiopyranyl group, a tetrahydrothiofuranyl group, and a 3-tetrahydrothiophene-1,1-dioxide group can be given.

As the group in which two or more of $R^2$, $R^3$, and $R^4$ bond to form a ring together with the sulfur atom in the formula (2), sulfonium cations shown by the formulas (2-47) to (2-63) described later can be given.

In the formula (3), as examples of the substituted or unsubstituted linear or branched alkyl group having 1 to 30 carbon atoms, the substituted or unsubstituted cyclic monovalent hydrocarbon group having 3 to 30 carbon atoms, the substituted or unsubstituted aryl group having 6 to 30 carbon atoms, or the unsubstituted monovalent heterocyclic organic group having 4 to 30 atoms represented by $R^5$ and the $R^6$, the same groups as mentioned above can be given.

As the group in which $R^5$ and $R^6$ bond to form a ring together with the sulfur atom in the formula (3), iodonium cations shown by the formulas (3-38) and (3-39) described later can be given.

[1-1] $M^+$ in the formula (1)

The site of the monovalent onium cation represented by $M^+$ in the formula (1) can be produced according to the general method described in, for example, Advances in Polymer Science, Vol. 62, p. 1 to 48 (1984).

As specific examples of the sulfonium cation shown by the formula (2) that can be preferably used, the sulfonium cations shown by the following formulas (2-1) to (2-64) can be given.

(2-1)
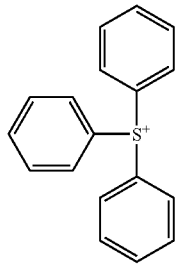

(2-2)
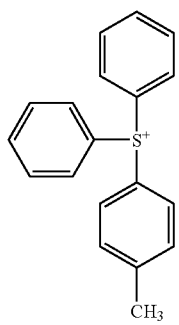

(2-3)
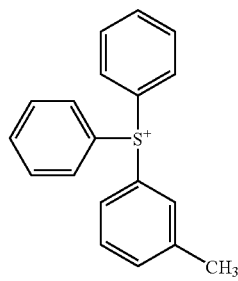

(2-4)
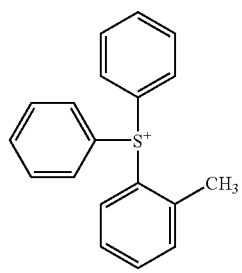

(2-5)
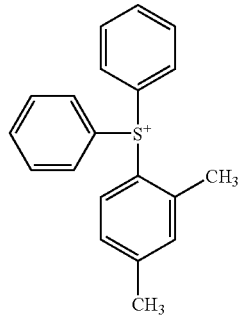

(2-6)
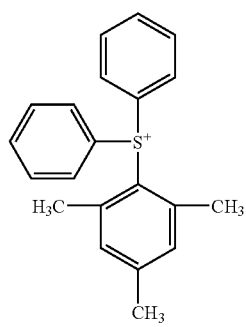

(2-7)
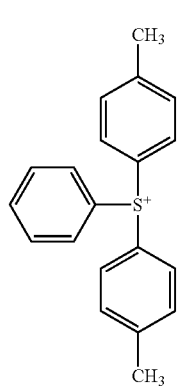

(2-8)
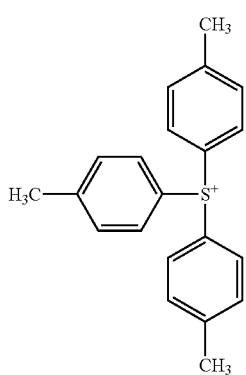
(2-9)
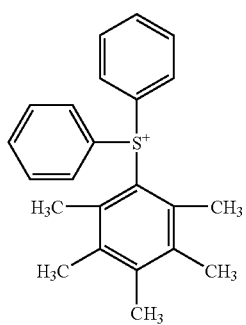
(2-10)
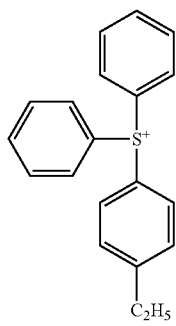
(2-11)
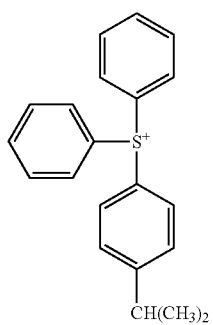
(2-12)
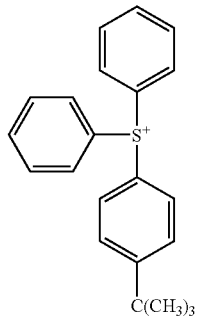
(2-13)
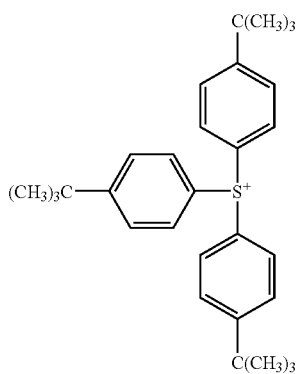
(2-14)
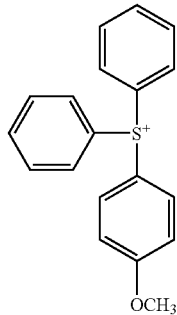
(2-15)
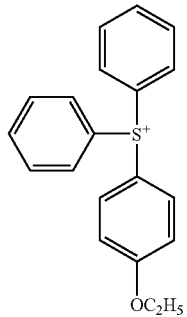
(2-16)
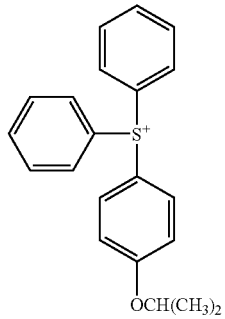

(2-17)
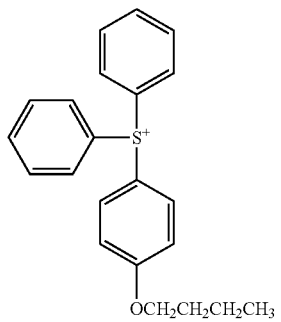
(2-18)
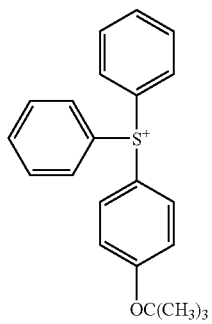
(2-19)
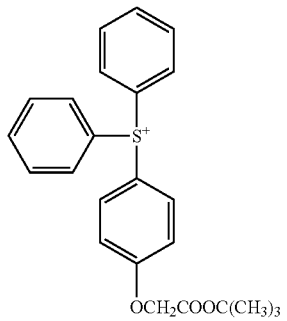
(2-20)
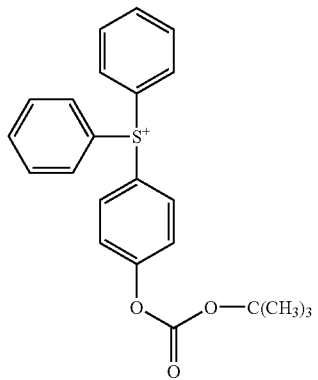
(2-21)
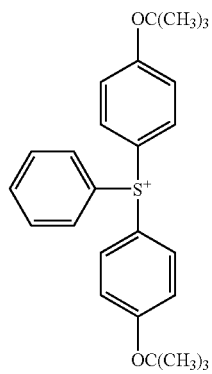
(2-22)
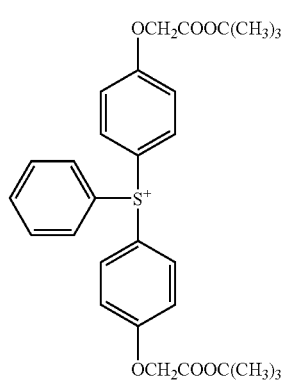
(2-23)
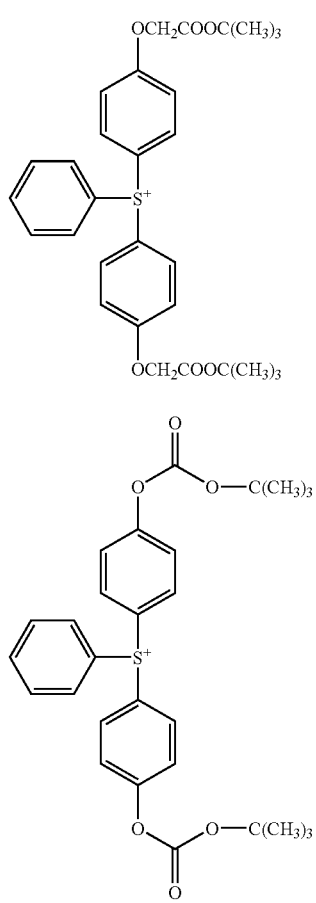
(2-24)
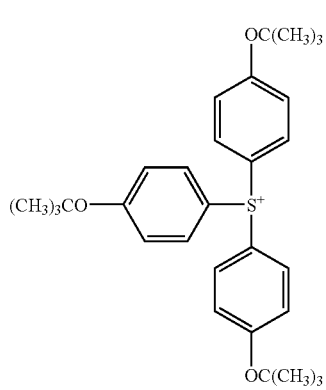

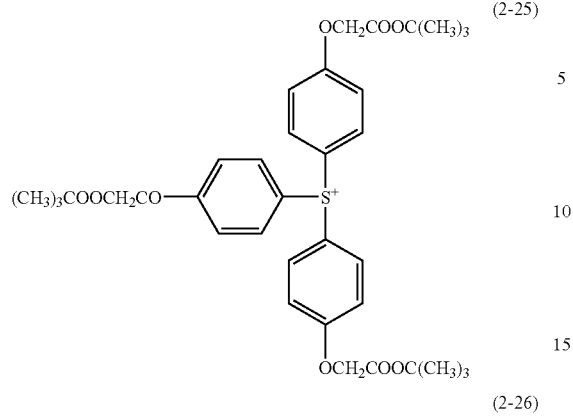
(2-25)
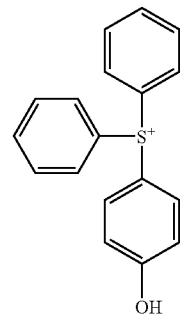
(2-26)
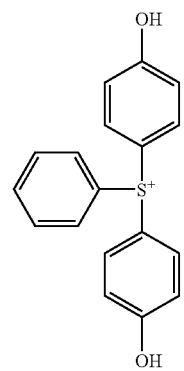
(2-27)
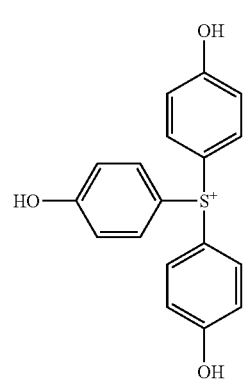
(2-28)
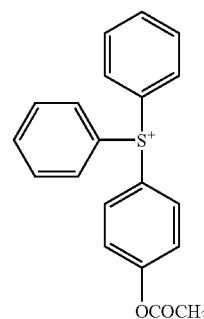
(2-29)
(2-30)
(2-31)
(2-32)
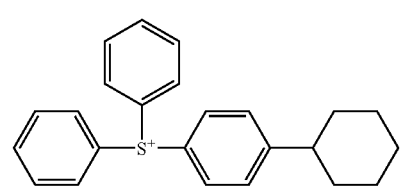
(2-33)

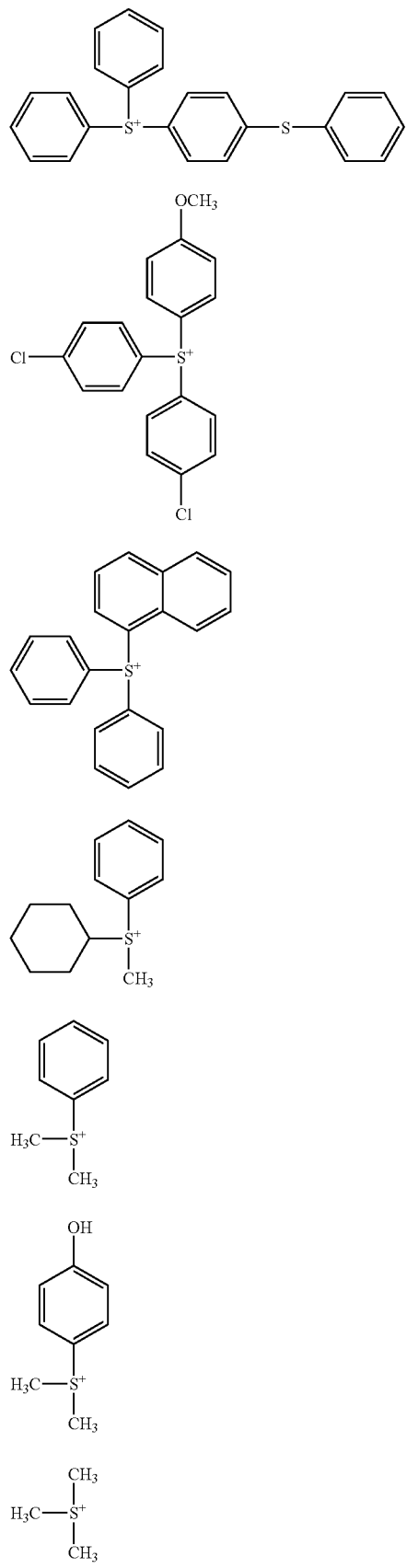
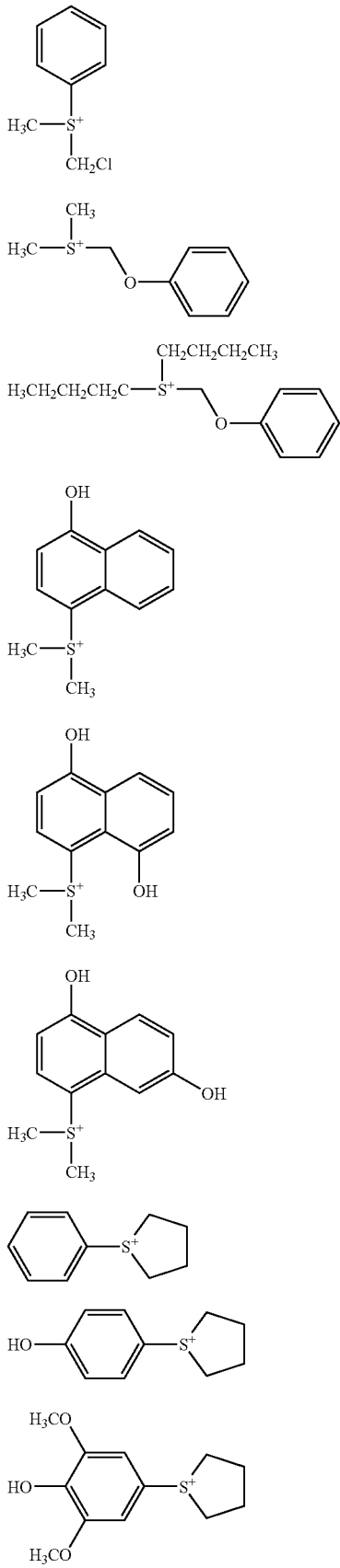

-continued
(2-50)
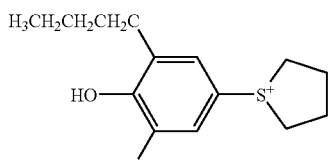
(2-51)
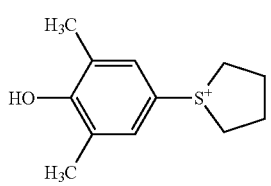
(2-52)
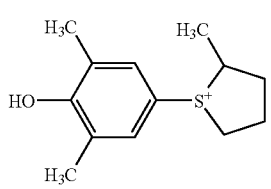
(2-53)
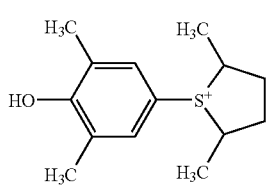
(2-54)
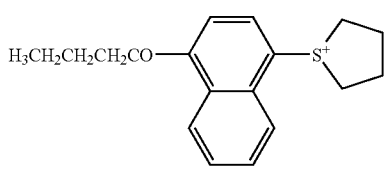
(2-55)
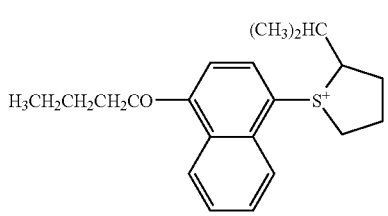
(2-56)
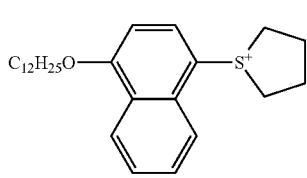
(2-57)
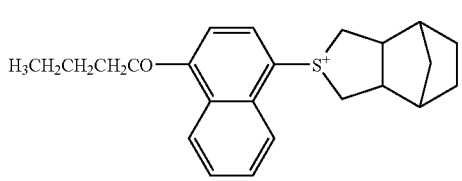
(2-58)
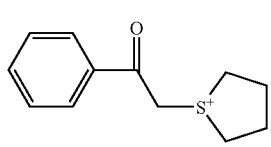
-continued
(2-59)
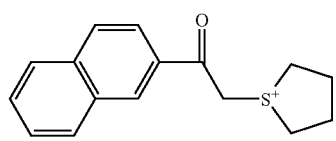
(2-60)
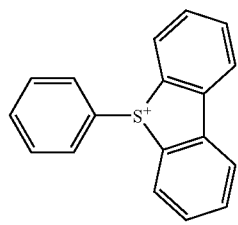
(2-61)
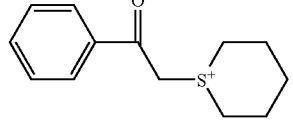
(2-62)
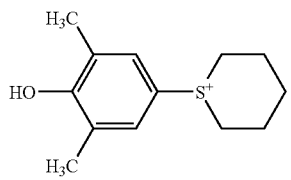
(2-63)
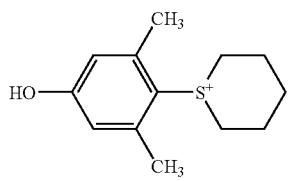
(2-64)
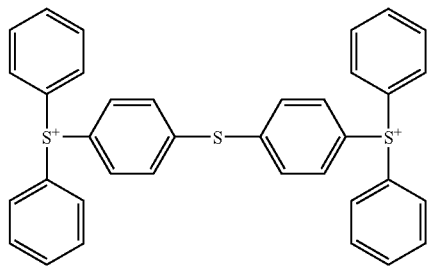
As specific examples of the iodonium cation shown by the formula (3) that can be preferably used, iodonium cations shown by the following formulas (3-1) to (3-39) can be given.
(3-1)
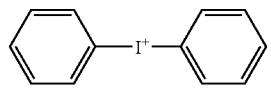
(3-2)
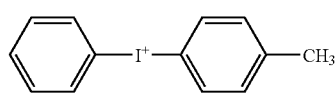
(3-3)
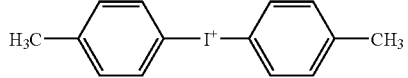

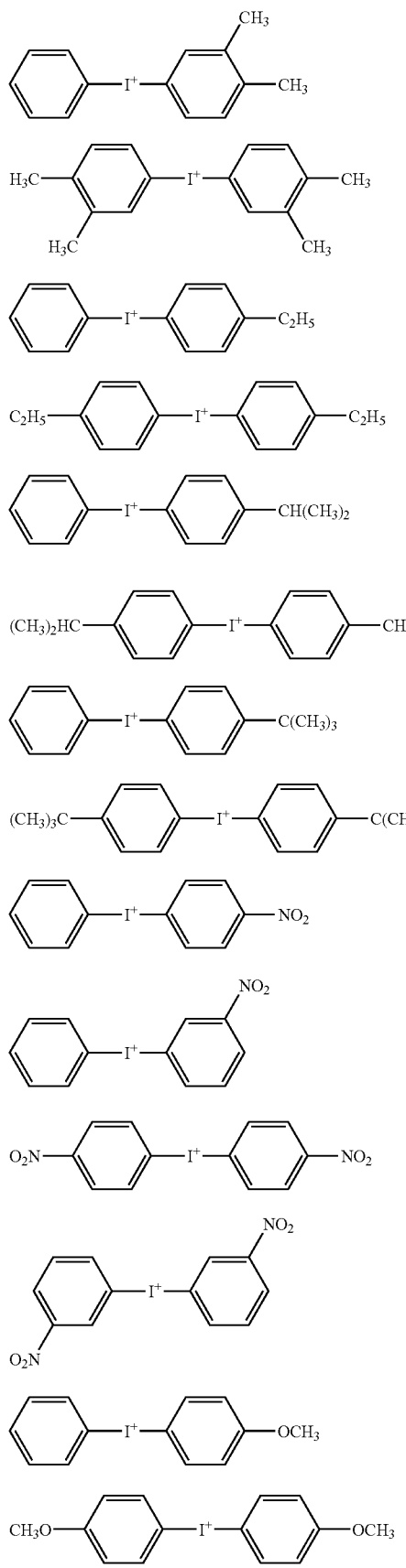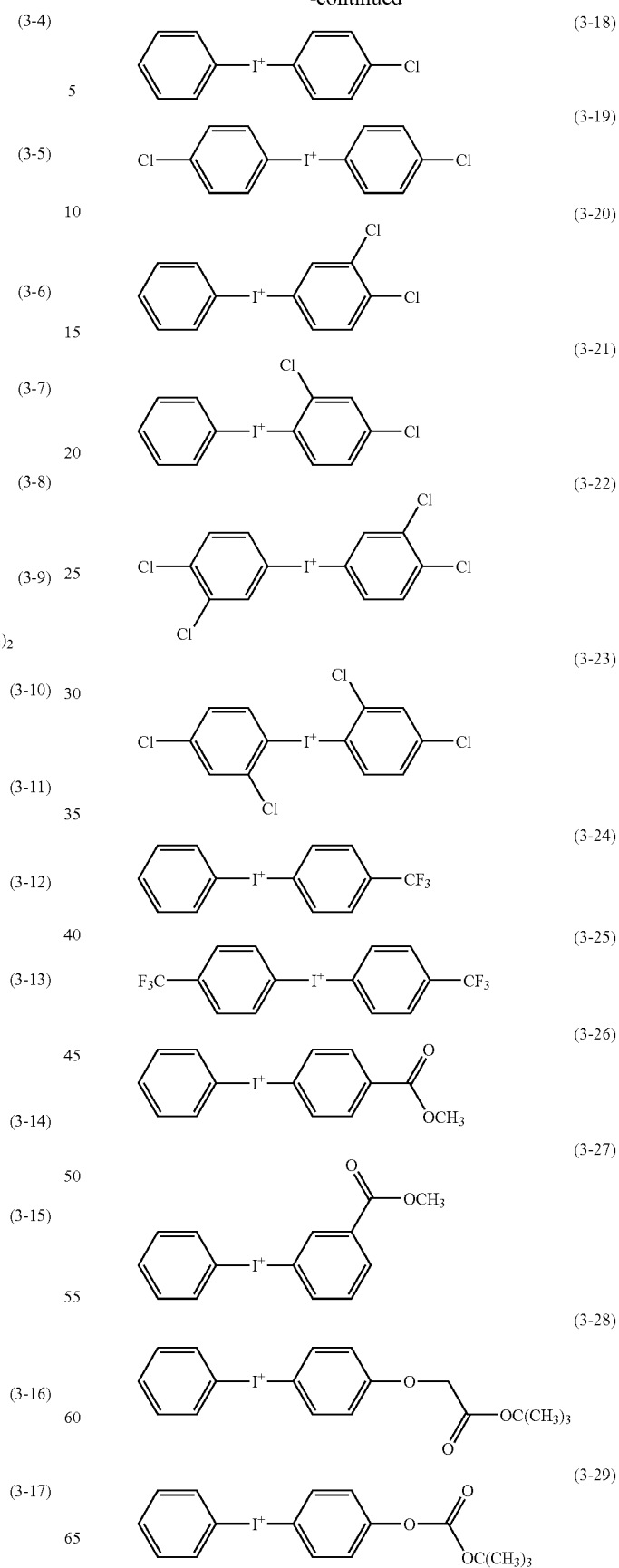

(3-30)
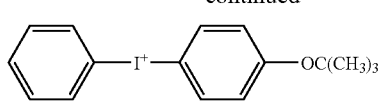

(3-31)
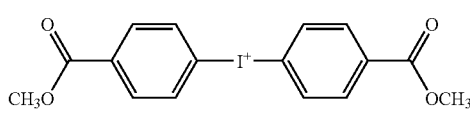

(3-32)

(3-33)
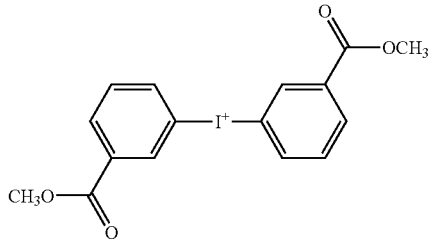

(3-34)
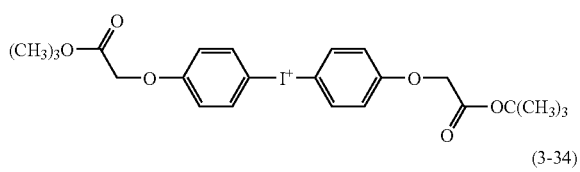

(3-35)
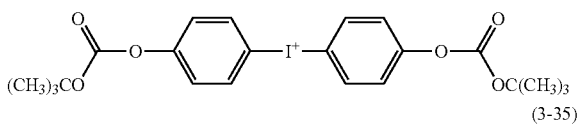

(3-36)
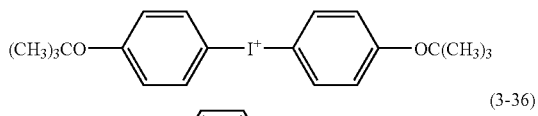

(3-37)
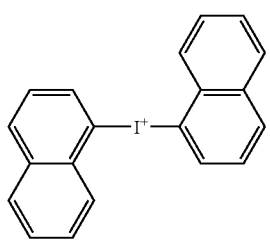

(3-38)
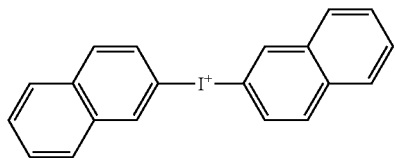

(3-39)
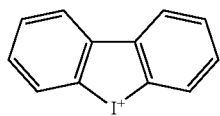

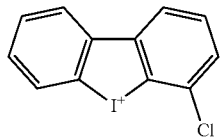

Among these monovalent onium cations (the sulfonium cations shown by the formula (2) and the iodonium cations shown by the formula (3)), the sulfonium cations shown by the formulas (2-1), (2-2), (2-6), (2-8), (2-13), (2-19), (2-25), (2-27), (2-29), (2-51), and (2-54) and the iodonium cations shown by the formulas (3-1) and (3-11) are preferable. The sulfonium cation shown by the formula (2-1), that is, a triphenylsulfonium cation, is particularly preferable.

The n in the formula (1) is an integer from 1 to 5, preferably 1 to 3, and more preferably 1 or 2.

The polymerizable onium sulfonate is preferably a compound shown by the following formula (1-1), specifically, triphenylsulfonium-1,1,2,2-tetrafluoro-4-(2-methylacryloyloxy)-butane-1-sulfonate.

(1-1)
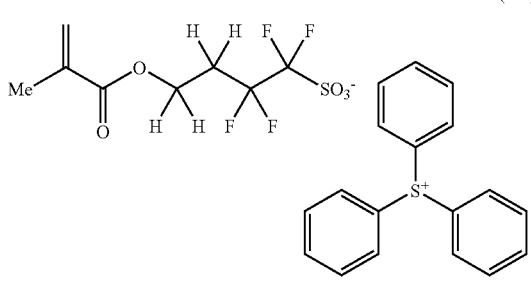

[2] Process for producing polymerizable onium sulfonate

The process for producing the polymerizable onium sulfonate of the present invention comprises a first step of sulfinating 4-bromo-3,3,4,4-tetrafluorobutan-1-ol using a sulfinating agent to obtain a metal sulfinate shown by the following formula (4), a second step of oxidizing the metal sulfinate using an oxidizer to obtain a metal sulfonate shown by the following formula (5), a third step of reacting the metal sulfonate with a monovalent onium salt shown by the following formula (6) to obtain an onium sulfonate shown by the following formula (7), and a fourth step of reacting the onium sulfonate with an alkyl acrylic acid halide shown by the following formula (8) or an alkyl acrylic acid anhydride shown by the following formula (9) to obtain a polymerizable onium sulfonate shown by the following formula (1-a).

(4)
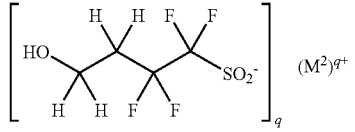

wherein $(M^2)^{q+}$ shows a counter cation that is a metal ion and q is an arbitrary integer.

As examples of the counter cation that is the metal ion of $(M^2)^{q+}$, lithium, sodium, potassium, and calcium can be given. q is preferably 1 or 2.

(5)
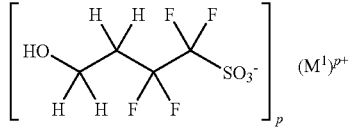

wherein $(M^1)^{p+}$ shows a counter cation that is a metal ion and p is an arbitrary integer.

As examples of the counter cation that is the metal ion of $(M^1)^{p+}$, lithium, sodium, potassium, and calcium can be given. p is preferably 1 or 2.

  (6)

wherein $M^+$ shows a sulfonium cation shown by the following formula (2) or an iodonium cation shown by the following formula (3) and $X^-$ shows a monovalent anion.

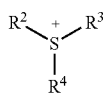  (2)

wherein $R^2$, $R^3$, and $R^4$ individually represent a substituted or unsubstituted linear or branched alkyl group having 1 to 30 carbon atoms, a substituted or unsubstituted monovalent cyclic hydrocarbon group having 3 to 30 carbon atoms, a substituted or unsubstituted aryl group having 6 to 30 carbon atoms, or an unsubstituted monovalent heterocyclic organic group having 4 to 30 atoms, or two or more of $R^2$, $R^3$, and $R^4$ may bond to form a ring together with the sulfur atom in the formula (2),

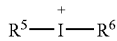  (3)

wherein $R^5$ and $R^6$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or $R^5$ and $R^6$ may bond to form a ring together with the iodine atom in the formula (3).

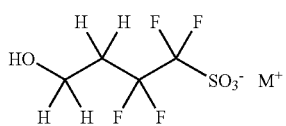  (7)

wherein $M^+$ is the same as $M^+$ in the formula (6).

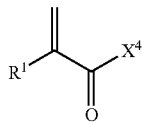  (8)

wherein $R^1$ represents a hydrogen atom, a fluorine atom, or an alkyl group having 1 to 3 carbon atoms, in which some or all of the hydrogen atoms may be substituted by a fluorine atom, $X^4$ represents a fluorine atom a chlorine atom, a bromine atom, or an iodine atom.

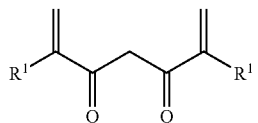  (9)

wherein $R^1$ is the same as the $R^1$ in the formula (8).

The onium sulfonate compound can be synthesized using a method conforming to the methods described in, for example, Advances in Polymer Science, Vol. 62, p. 1-48 (1984) and Inorganic Chemistry, Vol. 32, p. 5007-5011 (1993).

However, according to the method for producing the polymerizable onium sulfonate of the present invention, an onium sulfonate having a polymerizable site can be obtained. Several methods of producing the polymerizable onium sulfonate may be conceivable. As a result of extensive studies, the inventors of the present invention have found that the polymerizable onium sulfonate can be produced in high yield by a simple process comprising the first to fourth steps shown by the following reaction formula (a).

Reaction formula (a)

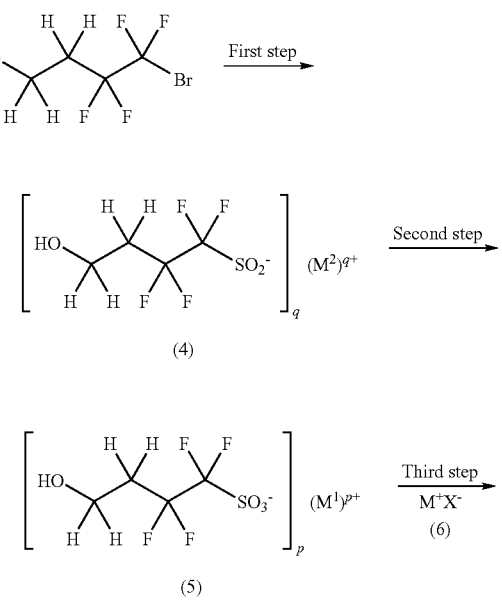

(4)

(5)

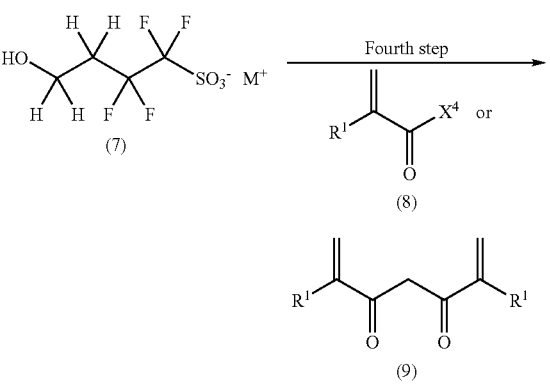

(7)

(8)

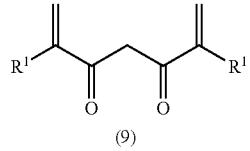

(9)

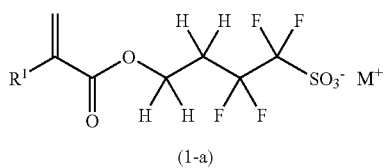

(1-a)

In the process for producing the polymerizable onium sulfonate of the present invention, it is important to carry out the four reaction steps consisting of the first to fourth steps shown in the order of the above reaction formula (a). It is difficult to produce the polymerizable onium sulfonate in any other order.

For example, the conversion reaction to the alkyl acrylate in the fourth step in the producing process of the present invention between the alcohols and the alkyl acrylic acid halide shown by the formula (8) or the alkyl acrylic acid anhydride shown by the formula (9) is usually carried out in a nonpolar solvent such as chloroform, dichloromethane, and toluene. However, since the metal sulfinate shown by the formula (4) obtained in the first step is insoluble in a nonpolar solvent such as toluene, it is difficult to proceed with the conversion reaction into an ester. The reaction does not proceed even if a polar solvent such as acetonitrile is used instead of the nonpolar solvent such as toluene. The following reaction formula (b) indicates that the metal sulfinate shown by the formula (4) cannot be converted into the alkyl acrylate by using the alkyl acrylic acid halide shown by the formula (8) or the alkyl acrylic acid anhydride shown by the formula (9).

Reaction formula (b)

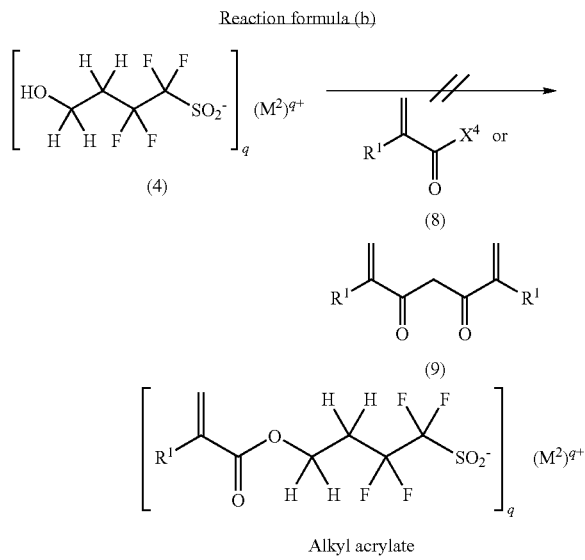

Alkyl acrylate

In addition, the onium sulfonate shown by the formula (7) obtained in the third step is insoluble in a nonpolar solvent and it is difficult to proceed with the "conversion reaction into an ester". The reaction does not proceed even if a polar solvent such as acetonitrile is used instead of the nonpolar solvent such as toluene. The following reaction formula (c) indicates that the onium sulfonate shown by the formula (7) cannot be converted into an ester by the reaction with the alkyl acrylic acid halide shown by the formula (8) or the alkyl acrylic acid anhydride shown by the formula (9).

Reaction formula (c)

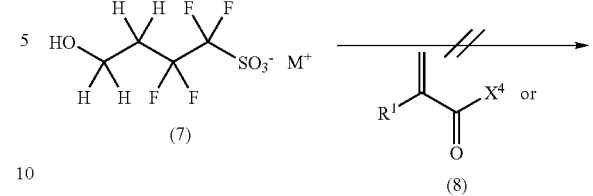

Alkyl acrylate

Furthermore, when an ion-exchange reaction into an onium salt (corresponding to the third step of the process of the present invention) is carried out after the first step without carrying out the second step, an "onium sulfinate" can be obtained. Since the "onium sulfinate" is soluble in a nonpolar solvent, the "conversion reaction into the alkyl acrylate (corresponding to the fourth step of the process of the present invention)" can succeedingly be carried out. An "alkyl acrylate" can be obtained in this manner. However, if the "alkyl acrylate" (polymerizable onium sulfinate) is caused to be present together with an "oxidizer" (corresponding to the second step of the process of the present invention) in order to obtain the polymerizable onium sulfonate from the "alkyl acrylate", an extensive decomposition reaction takes place. Therefore, it is difficult to obtain a polymerizable onium sulfonate if the second step is omitted after the first step.

The following reaction formula (d) indicates that if the metal sulfinate shown by the formula (4) is reacted with the monovalent onium salt shown by the formula (6) to obtain an onium sulfinate shown by the formula (7), the resulting onium sulfinate shown by the formula (7) is reacted with the alkyl acrylic acid halide shown by the formula (8) or the alkyl acrylic acid anhydride shown by the formula (9) to obtain an alkyl acrylate, and the resulting alkyl acrylate is caused to be present together with an oxidizer, the alkyl acrylate is decomposed.

Reaction formula (d)

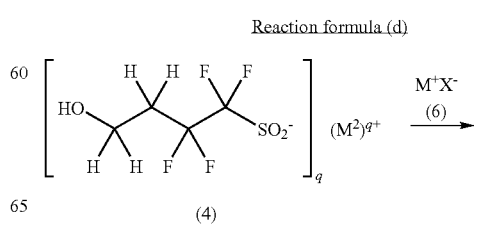

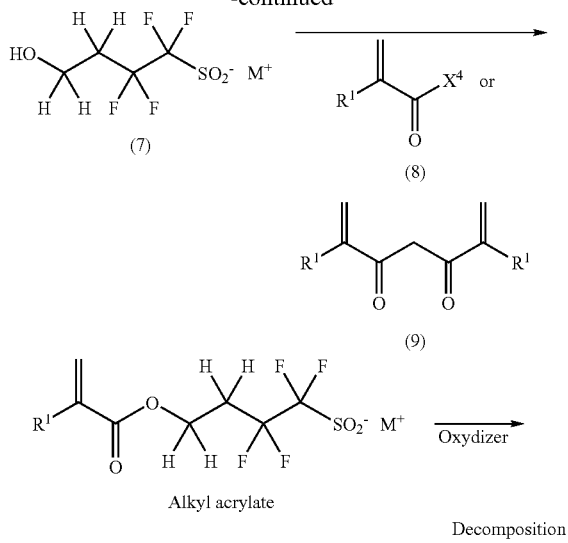

Alkyl acrylate

Decomposition

On the other hand, the above decomposition reaction can be suppressed according to the process for producing the polymerizable onium sulfonate of the present invention in which the first, second, third, and fourth steps are carried out in this order. Therefore, the polymerizable onium sulfonate shown by the formula (1-a) can be obtained in good yield. For this reason, it is very important for the process for producing the polymerizable onium sulfonate of the present invention to follow the order of the first, second, third, and fourth steps.

Each of the first step, the second step, the third step, and the fourth step is now described in detail.

[2-1] First Step The first step is described below. This is a step of sulfinating 4-bromo-3,3,4,4-tetrafluorobutan-1-ol using a sulfinating agent to obtain the metal sulfinate shown by the formula (4).

As examples of the sulfinating agent, lithium dithionite, sodium dithionite, potassium dithionite, ammonium dithionite, sodium hydroxymethanesulfinate, zinc hydroxymethanesulfinate, sodium sulfite, potassium sulfite, sodium hydrogensulfite, and potassium hydrogensulfite can be given. Of these, sodium dithionite and potassium dithionite are preferable, with sodium dithionite being particularly preferable. The counter cation that is the metal ion of the polymerizable onium sulfonate shown by the formula (1-a) is derived from the sulfinating agent.

The molar ratio of the sodium dithionite to the 4-bromo-3,3,4,4-tetrafluorobutan-1-ol used in the first step is preferably 0.5 to 10, more preferably 0.9 to 5.0, and particularly preferably 1.0 to 2.0.

The reaction of the first step can be accelerated by adding an inorganic base. As examples of the inorganic base, lithium carbonate, sodium carbonate, potassium carbonate, lithium hydrogencarbonate, sodium hydrogencarbonate, and potassium hydrogencarbonate can be given. Among these, sodium hydrogencarbonate, potassium hydrogencarbonate, and the like are preferable. The molar ratio of the inorganic base to the sodium dithionite is preferably 0.1 to 10.0, and more preferably 1.0 to 3.0.

The reaction of the first step is preferably carried out in a mixed solvent of an organic solvent and water. As the organic solvent, lower alcohols, tetrahydrofuran, N,N-dimethylformamide, N,N-dimethylacetamide, acetonitrile, dimethylsulfoxide, and the like are preferable from the viewpoint of mutual solubility with water. N,N-dimethylacetamide, acetonitrile, dimethylsulfoxide, and the like are more preferable, with a particularly preferable solvent being acetonitrile.

The amount of the organic solvent used is preferably 5 parts by mass or more, more preferably 10 parts by mass or more, and particularly preferably 20 to 90 parts by mass for 100 parts by mass of the total of the organic solvent and water.

The reaction temperature is preferably 40 to 200° C., and more preferably 60 to 100° C. The reaction time is preferably 0.5 to 72 hours, and more preferably 2 to 24 hours. When the reaction temperature is higher than the boiling point of the organic solvent or water, a pressure-resistant vessel such as an autoclave is preferably used.

[2-2] Second Step

The second step is described below. In this step, the metal sulfinate obtained in the first step is oxidized using an oxidizer to obtain the metal sulfonate shown by the formula (5). As examples of the oxidizer used for oxidizing the metal sulfinate, hydrogen peroxide, metachloroperbenzoate, t-butyl hydroperoxide, potassium peroxysulfate, potassium permanganate, sodium perborate, sodium metaiodate, chromic acid, sodium dichromate, halogen, iodobenzene dichloride, iodobenzene diacetate, osmium (VIII) oxide, ruthenium (VIII) oxide, sodium hypochlorite, sodium chlorite, oxygen gas, and ozone gas can be given. Among these, hydrogen peroxide, metachloroperbenzoate, t-butyl hydroperoxide, and the like are preferable.

The molar ratio of the oxidizer to the metal sulfinate is preferably 0.9 to 10.0, and more preferably 1.0 to 2.0.

A transition metal catalyst may be used together with the oxidizer. As examples of the transition metal catalyst, disodium tungstate, iron (III) chloride, ruthenium (III) chloride, and selenium (IV) oxide can be given. Among these, disodium tungstate is preferable. The molar ratio of the transition metal catalyst to the metal sulfinate is preferably 0.0001 to 1.0, more preferably 0.001 to 0.5, and particularly preferably 0.001 to 0.1.

In addition to the oxidizer and the transition metal catalyst, a buffering agent may be used in order to adjust the pH of the reaction solution. As examples of the buffering agent, disodium hydrogenphosphate, sodium dihydrogenphosphate, dipotassium hydrogenphosphate, and potassium dihydrogenphosphate can be given. The molar ratio of the buffering agent to the metal sulfinate is preferably 0.01 to 2.0, more preferably 0.03 to 1.0, and particularly preferably 0.05 to 0.5.

The reaction of this step is usually carried out in a solvent. Examples of the reaction solvent that can be preferably used include water and organic solvents such as lower alcohols, tetrahydrofuran, N,N-dimethylformamide, N,N-dimethylacetamide, acetonitrile, dimethylsulfoxide, acetic acid, and trifluoroacetic acid. Of these, water, methanol, N,N-dimethylacetamide, acetonitrile, and dimethylsulfoxide are preferable, with water and methanol being particularly preferable.

The amount of the reaction solvent used is preferably 5 to 100 parts by mass, more preferably 10 to 100 parts by mass, and particularly preferably 20 to 50 parts by mass for 100 parts by mass of the metal sulfinate.

As required, a mixture of water and the above-mentioned organic solvent may be used. When the organic solvent, the amount of the organic solvent is preferably 5 parts by mass or more, more preferably 10 parts by mass, and particularly preferably 20 to 90 parts by mass for 100 parts by mass of the total of the organic solvent and water.

The reaction temperature of this step is preferably 0 to 100° C., more preferably 5 to 60° C., and particularly preferably 5 to 40° C. The reaction time is preferably 0.1 to 72 hours, more preferably 0.5 to 24 hours, and particularly preferably 0.5 to 12 hours.

[2-3] Third Step

The third step is described below. In the third step, the metal sulfonate shown by the formula (5) obtained in the second step is converted into the onium sulfonate of the formula (7) by the ion exchange reaction with a monovalent onium salt (counter ion-exchange precursor) shown by the formula (6). The ion-exchange reaction of the metal sulfonate of the formula (5) can be carried out by ion-exchange chromatography according to the general method described in, for example, Advances in Polymer Science, Vol. 62, p. 1-48 (1984). The process according to the method described later in Example 1 may also be used.

As examples of the monovalent onium salt (counter ion-exchange precursor) shown by the formula (6), a sulfonium salt shown by the following formula (11) and an iodonium salt shown by the following formula (12) can be given.

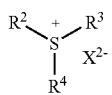
(11)

wherein $X^{2-}$ is a monovalent anion and $R^2$, $R^3$, and $R^4$ are the same as $R^2$, $R^3$, and $R^4$ in the formula (2).

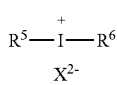
(12)

wherein $X^{2-}$ is the same as $X^{2-}$ in the formula (11) and $R^5$ and $R^6$ are the same as $R^5$ and $R^6$ in the formula (3).

As examples of the onium cations in the formulas (11) and (12), the above-mentioned onium cations can be given. As examples of $X^{2-}$ in the formula (11) and formula (12), $F^-$, $Cl^-$, $Br^-$, $I^-$, $ClO_4^-$, $HSO_4^-$, $H_2PO_4^-$, $BF_4^-$, $PF_6^-$, $SbF_6^-$, aliphatic sulfonate anion, aromatic sulfonate anion, trifluoromethanesulfonate anion, fluorosulfonate anion, aliphatic carboxylate anion, aromatic carboxylate anion, fluorocarboxylate anion, and trifluoroacetate anion can be given. Of these, $Cl^-$, $Br^-$, $HSO_4^-$, $BF_4^-$, and aliphatic sulfonate ion are preferable, with $Cl^-$, $Br^-$, and $HSO_4^-$ being more preferable.

The molar ratio of the counter ion-exchange precursor to the metal sulfonate is preferably 0.5 to 10.0, more preferably 0.8 to 2.0, and particularly preferably 0.9 to 1.2.

The reaction of this step is usually carried out in a solvent.

The same solvents mentioned above can be used in this step. The amount of the reaction solvent used is preferably 5 to 100 parts by mass, more preferably 10 to 100 parts by mass, and particularly preferably 20 to 50 parts by mass for 100 parts by mass of the counter-ion exchange precursor. As required, a mixture of water and the above-mentioned organic solvent may be used. The reaction temperature in this step is preferably 0 to 80° C., and more preferably 5 to 30° C. The reaction time is preferably 10 minutes to 16 hours, and more preferably 30 minutes to six hours.

The onium sulfonate shown by the formula (7) obtained in this manner may be purified by extracting with an organic solvent, as required. As the reaction solvent, organic solvents which are immiscible with water are preferable. Examples of such organic solvents include esters such as ethyl acetate and n-butyl acetate; ethers such as diethyl ether; alkyl halides such as methylene chloride and chloroform; and the like.

[2-4] Fourth Step

The fourth step is described below. In the fourth step, the onium sulfonate shown by the formula (7) obtained in the third step is converted into an alkyl acrylate using the alkyl acrylic acid halide shown by the formula (8) or the alkyl acrylic acid anhydride shown by the formula (9) to obtain the polymerizable onium sulfonate shown by the formula (1-a).

As specific examples of the alkyl acrylic acid halide and the alkyl acrylic acid anhydride used, acrylic acid fluoride, acrylic acid chloride, acrylic acid bromide, acrylic acid iodide, acrylic acid anhydride, methacrylic acid fluoride, methacrylic acid chloride, methacrylic acid bromide, methacrylic acid iodide, methacrylic acid anhydride, trifluoromethacrylic acid fluoride, trifluoromethacrylic acid chloride, trifluoromethacrylic acid bromide, trifluoromethacrylic acid iodide, and trifluoromethacrylic acid anhydride can be given. Of these, acrylic acid chloride, acrylic acid anhydride, methacrylic acid chloride, methacrylic acid anhydride, trifluoromethacrylic acid chloride, trifluoromethacrylic acid anhydride are preferable, with methacrylic acid chloride and methacrylic acid anhydride being particularly preferable.

The amount of the alkyl acrylic acid halide or the alkyl acrylic acid anhydride used is preferably 0.5 to 3.0 mol, more preferably 0.7 to 2.0 mol, and particularly preferably 1.0 to 1.6 mol for one mol of the onium sulfonate. If the amount of the alkyl acrylic acid halide and the alkyl acrylic acid anhydride used is less than 0.5 mol, the reaction selectivity and the yield of the target compound may decrease. If more than 3.0 mol, the amount of the alkyl acrylic acid halide and the alkyl acrylic acid anhydride not involved in the reaction increases, resulting in a cost increase and an increase in the burden to environment due to an increase in the amount of waste materials.

Additives may be added to accelerate the reaction of this step. The reaction temperature may be lowered by adding an additive. Lowering the reaction temperature is effective for suppressing production of byproducts. As the additives, at least one acid selected from the group consisting of organic sulfonic acids such as methanesulfonic acid, ethanesulfonic acid, p-toluenesulfonic acid, benzenesulfonic acid, and trifluoromethanesulfonic acid and Lewis acids such as boron trifluoride, titanium tetrachloride, and tin tetrachloride can be suitably used.

The amount of the additive per one mol of the substituted onium sulfonate which is the substrate is preferably 0.001 to 5.0 mol, more preferably 0.01 to 2.0 mol, and particularly preferably 0.1 to 1.0 mol. The reaction temperature in this step is preferably 0 to 200° C., more preferably 20 to 100° C., and particularly preferably 30 to 80° C. If the reaction temperature is less than 0° C., the reaction rate is unduly retarded. The producing process at such a low temperature may be impracticable. If the reaction temperature is higher than 200° C., the alkyl acrylic acid halide and alkyl acrylic acid anhydride raw materials or the polymerizable onium sulfonate product may polymerize.

Although the reaction in this step can be carried out without using a solvent, the reaction is usually carried out in a solvent. As the reaction solvent, aromatic solvents such as benzene, toluene, xylene, and mesitylene; ether solvents such as diethyl ether, methyl t-butyl ether, diisopropyl ether, and tetrahydrofuran; and halogen-containing solvents such as methylene chloride, chloroform, and carbon tetrachloride are preferable. A halogen-containing solvent such as methylene chloride, chloroform, and carbon tetrachloride are more preferable, with chloroform being particularly preferable.

When the solvent is used, the amount of the solvent per 1 g of the onium sulfonate is preferably 0.2 to 50 g, more preferably 0.5 to 20 g, and particularly preferably 1.0 to 10 g. If the amount of the solvent is less than 0.2 g, the onium sulfonate may be dissolved only insufficiently. If more than 50 g, the productivity is impaired and the production cost may increase.

A polymerization inhibitor may be added in order to prevent polymerization of the alkyl acrylic acid halide and alkyl acrylic acid anhydride raw materials or the polymerizable onium sulfonate product. Examples of the polymerization inhibitor include 2,5-di-t-butylhydroquinone, 1,2,4-trihydroxybenzene, 2,5-bistetramethylbutylhydroquinone, leucoquinizarin, N,N'-di-2-naphthyl-p-phenylenediamine, N,N'-dinaphtyl-p-phenylenediamine, 4,4'-bis(α,α'-dimethylbenzyl)diphenylamine, 4,4'-dicumyl-diphenylamine, 2,2'-methylenebis(4-methyl-6-tert-butylphenol), N-(1-methylheptyl)-N'-phenyl-p-phenylenediamine, phenothiazine, 2-methoxyphenothiazine, tetraethylthiuram disulfide, 1,1-diphenyl-2-picrylhydrazyl, 1,1-diphenyl-2-picrylhydrazine, N-nitrosophenylhydroxylamine, and aluminum salt of N-nitrosophenylhydroxylamine.

As commercially available polymerization inhibitors which are sold under following trade names, Nonflex F (N,N'-di-2-naphthyl-p-phenylenediamine), Nonflex H (N,N'-dinaphtyl-p-phenylenediamine), Nonflex DCD (4,4'-bis(α,α'-dimethylbenzyl)diphenylamine, 4,4'-dicumyl-diphenylamine), Nonflex MBP (2,2'-methylenebis(4-methyl-6-tert-butylphenol), and Ozonon 35 (N-(1-methylheptyl)-N'-phenyl-p-phenylenediamine), all manufactured by Seiko Chemical Co., Ltd., Q-1300 (N-nitrosophenylhydroxylamine) and Q-1301 (aluminum salt of N-nitrosophenylhydroxylamine), both manufactured by Wako Pure Chemical Industries, Ltd., and the like can be given.

The above commercially available polymerization inhibitor products are easily available. The amount of the polymerization inhibitor used in the process of the present invention per one mol of the onium sulfonate which is the raw material is preferably 0.000005 to 0.1 mol, more preferably 0.00001 to 0.05 mol, and particularly preferably 0.0001 to 0.03 mol. If the amount of the polymerization inhibitor is less than 0.000005 mol, a sufficient effect of inhibiting the polymerization cannot be obtained, causing polymerization of alkyl acrylic acid halide or alkyl acrylic anhydride raw materials or the polymerizable onium sulfonate product. On the other hand, an amount larger than 0.1 mol only results in a cost increase because no significant difference in the performance of inhibiting the polymerization is brought about by using such an excess amount.

The polymerizable onium sulfonate obtained in this manner may be purified by extracting with an organic solvent, as required. As the reaction solvent, organic solvents which are immiscible with water are preferable. Examples of such organic solvents include esters such as ethyl acetate and n-butyl acetate; ethers such as diethyl ether; alkyl halides such as methylene chloride and chloroform; and the like.

[3] Resin

The resin of the present invention has a repeating unit shown by the following formula (10). Because the onium salt moiety of the repeating unit shown by the following formula (10) functions as an acid generator, the resin of the present invention generates an acid, specifically sulfonic acid, when exposed to radiation or heat. This resin is extremely useful as a radiation sensitive acid generator in the radiation-sensitive resin composition described later.

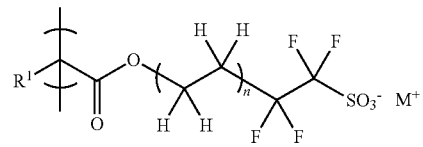

(10)

wherein $R^1$ represents a hydrogen atom, a fluorine atom, or an alkyl group having 1 to 3 carbon atoms, in which some or all of the hydrogen atoms may be substituted by a fluorine atom, $M^+$ represents a sulfonium cation shown by the following formula (2) or an iodonium cation shown by the following formula (3), and n represents an integer from 1 to 5.

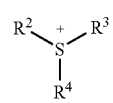

(2)

wherein $R^2$, $R^3$, and $R^4$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or two or more of $R^2$, $R^3$, and $R^4$ may bond to form a ring together with the sulfur atom in the formula (2).

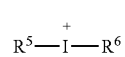

(3)

wherein $R^5$ and $R^6$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or $R^5$ and $R^6$ may bond to form a ring together with the iodine atom in the formula (3).

The repeating unit shown by the formula (10) forms a radiation-sensitive resin together with other repeating units which contain acid-unstable groups. As a result of exposure to radiation or heat, the resin generates the sulfonic acid shown by the following formula (10a),

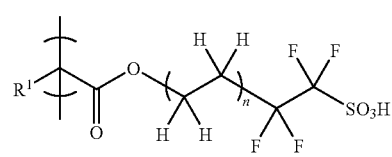

(10a)

wherein $R^1$ represents a hydrogen atom, a fluorine atom, or an alkyl group having 1 to 3 carbon atoms, in which some or all of the hydrogen atoms may be substituted by a fluorine atom, and n is an integer from 1 to 5.

Since the resin of the present invention has a fluorine-containing strong electron withdrawing group at the α-position of the sulfonyl group in its structure, the sulfonic acid shown by the formula (10a) which is produced by exposure to radiation or heat has a high acidity. Since fixed in the radiation sensitive resin composition, the resin of the present invention has a high boiling point and is volatilized only with difficulty during a lithographic process. The acid produced has a short diffusion length, that is, has an appropriate diffusion length in a resist coating film. In addition, since the fluorine atom content in the sulfonic acid shown by the formula (10a) is smaller than that of higher perfluoroalkane sulfonic acids, the resin exhibits the effect of low accumulability in the human body in addition to good combustibility.

In the formula (10), $R^1$ represents a hydrogen atom, a fluorine atom, or an alkyl group having 1 to 3 carbon atoms, in which some or all of the hydrogen atoms may be substituted by a fluorine atom. Among these, a hydrogen atom, a fluorine atom, a methyl group, and a trifluoromethyl group are preferable, with a methyl group being particularly preferable. As examples of the alkyl group having 1 to 3 carbon atoms represented by $R^1$, a methyl group, an ethyl group, a 1-propyl group, a 2-propyl group, a monofluoromethyl group, a difluoromethyl group, and a trifluoromethyl group can be given.

[3-1] Other Repeating Units

In addition to the repeating unit shown by the formula (10), the resin of the present invention may contain a repeating unit derived from the monomer shown by the following formula (13), for example. Such a repeating unit may be hereinafter referred to from time to time as "other repeating unit (13)".

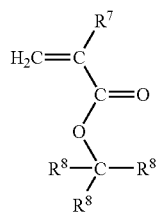

(13)

wherein $R^7$ represents a hydrogen atom, a methyl group, or a trifluoromethyl group and $R^8$ individually represent a monovalent alicyclic hydrocarbon group having 4 to 20 carbon atoms or a derivative thereof, or a linear or branched alkyl group having 1 to 4 carbon atoms, with a proviso that at least one of the three $R^8$s is an alicyclic hydrocarbon group having 4 to 20 carbon atoms or a derivative thereof, and that any two of the $R^8$s may form, in combination and together with the carbon atom to which the $R^8$s bond, a divalent alicyclic hydrocarbon group having 4 to 20 carbon atoms or a derivative thereof, with the remaining $R^8$ being a linear or branched alkyl group having 1 to 4 carbon atoms or a monovalent alicyclic hydrocarbon group having 4 to 20 carbon atoms or a derivative thereof.

Examples of the monovalent alicyclic hydrocarbon group having 4 to 20 carbon atoms include groups having an alicyclic ring derived from cycloalkanes such as norbornane, tricyclodecane, tetracyclododecane, adamantane, cyclobutane, cyclopentane, cyclohexane, cycloheptane, and cyclooctane. Examples of the $R^8$ include groups obtained by substituting the above group having an alicyclic ring with one or more of the linear, branched, or cyclic alkyl groups having 1 to 4 carbon atoms such as a methyl group, an ethyl group, an n-propyl group, an i-propyl group, an n-butyl group, a 2-methylpropyl group, a 1-methylpropyl group, and a t-butyl group. Among these alicyclic hydrocarbon groups, groups derived from an alicyclic ring such as norbornane, tricyclodecane, tetracyclododecane, adamantane, cyclopentane, or cyclohexane, and a group obtained by substituting the group having these alicyclic rings with the above-mentioned alkyl groups are preferable.

As examples of the derivatives of the above alicyclic hydrocarbon groups, groups having the above-alicyclic rings substituted with one or more substituents such as a hydroxyl group; a carboxyl group; an oxo group (=O group); hydroxyalkyl groups having 1 to 4 carbon atoms such as a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group, and a 4-hydroxybutyl group; alkoxyl groups having 1-4 carbon atoms such as a methoxy group, an ethoxy group, an n-propoxy group, an i-propoxy group, an n-butoxy group, a 2-methylpropoxy group, a 1-methylpropoxy group, and a t-butoxy group; a cyano group; and cyanoalkyl groups having 2 to 5 carbon atoms such as a cyanomethyl group, a 2-cyanoethyl group, a 3-cyanopropyl group, and a 4-cyanobutyl group can be given. Among the above substituents, a hydroxyl group, a carboxyl group, a hydroxymethyl group, a cyano group, a cyanomethyl group, and the like are preferable.

As examples of the linear or branched alkyl group having 1 to 4 carbon atoms represented by $R^8$, a methyl group, an ethyl group, an n-propyl group, an i-propyl group, an n-butyl group, a 2-methylpropyl group, a 1-methylpropyl group, and a t-butyl group can be given. Of these alkyl groups, a methyl group or an ethyl group are preferable.

As examples of the divalent alicyclic hydrocarbon group having 4 to 20 carbon atoms formed by bonding of any of the two $R^8$s together with the carbon atom to which the two $R^8$s bond, alicyclic groups derived from cycloalkanes such as norbornane, tricyclodecane, tetracyclododecane, adamantane, cyclobutane, cyclopentane, cyclohexane, cycloheptane, and cyclooctane can be given.

The group —COOC($R^8$)$_3$ in the formula (13) forms a carboxyl group by dissociating a part thereof by the action of an acid. As examples of the group —C($R^8$)$_3$ in the group —COOC($R^8$)$_3$, the groups shown by the following formulas (13a), (13b), (13c), and (13d) can be given.

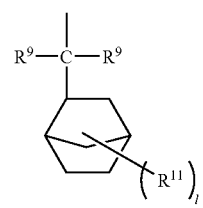

(13a)

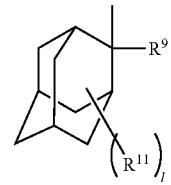

(13b)

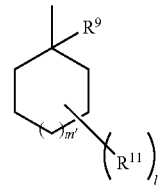

(13c)

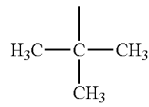

(13d)

wherein $R^9$ individually represent a linear or branched alkyl group having 1 to 4 carbon atoms, $R^{11}$ represents a substituted or unsubstituted alkyl group having 1 to 4 carbon atoms, an alkoxy group, or a cyano group, wherein two or more $R^{11}$s may be the same or different and two or more $R^{11}$s may bond with each other to form a ring structure having 3 to 8 carbon atoms together with the carbon atom to which the two $R^{11}$s bond, l is an integer from 0 to 4, and m' is 0 or 1.

As examples of the linear or branched alkyl group having 1 to 4 carbon atoms represented by $R^9$, a methyl group, an ethyl group, an n-propyl group, an i-propyl group, an n-butyl group, a 2-methylpropyl group, a 1-methylpropyl group, and a t-butyl group can be given. Of these alkyl groups, a methyl group or an ethyl group is preferable.

Among the groups shown by the formula (13a), a group having a methyl group for both of the two $R^9$s is preferable. As the group shown by the formula (13b), a group having a methyl group or an ethyl group for $R^9$ is particularly preferable. As the formula (13c), a group in which m'=0 and $R^9$ is a methyl group, a group in which m'=0 and $R^9$ is an ethyl group, a group in which m'=1 and $R^9$ is a methyl group, and a group in which m'=1 and $R^9$ is an ethyl group are preferable.

The following groups can be given as specific examples of the group shown by the formula (13a), the group shown by the formula (13b), and the group shown by the formula (13c).

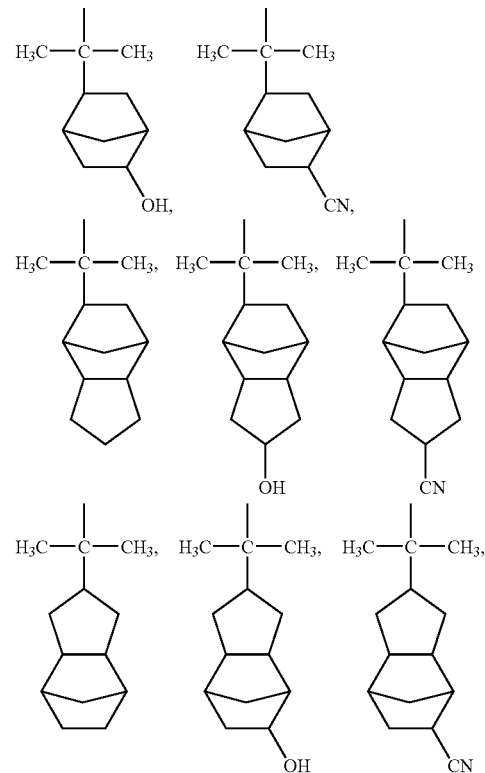

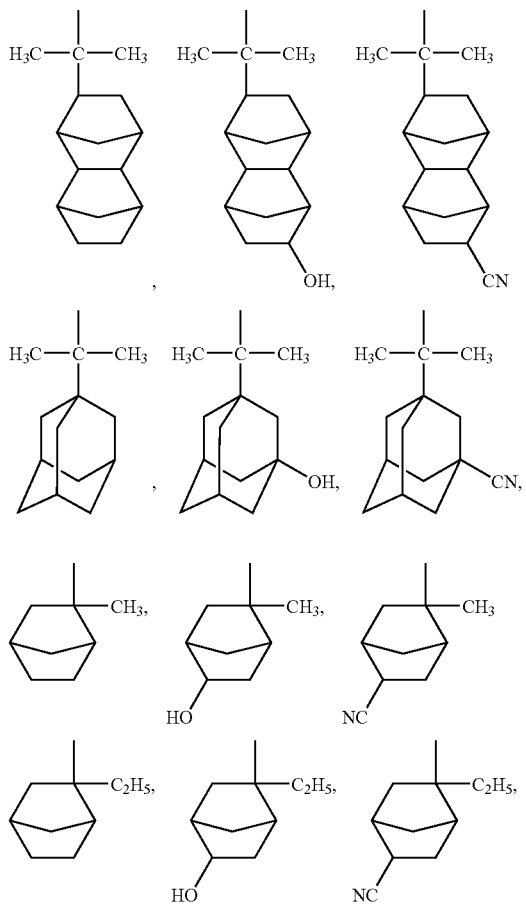

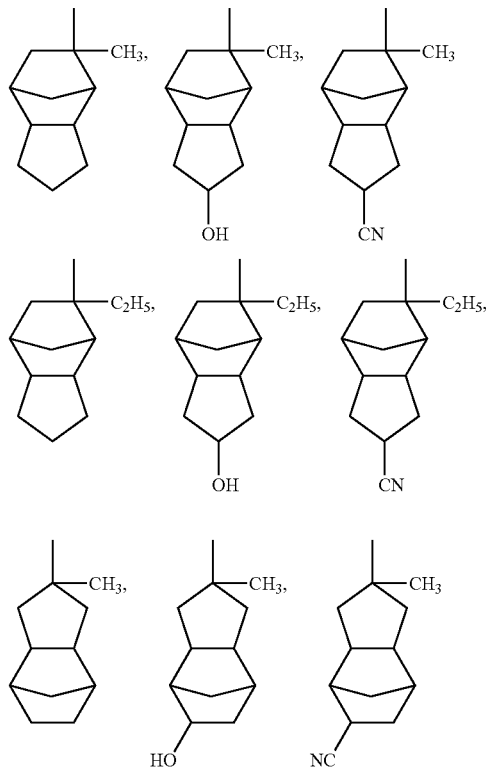

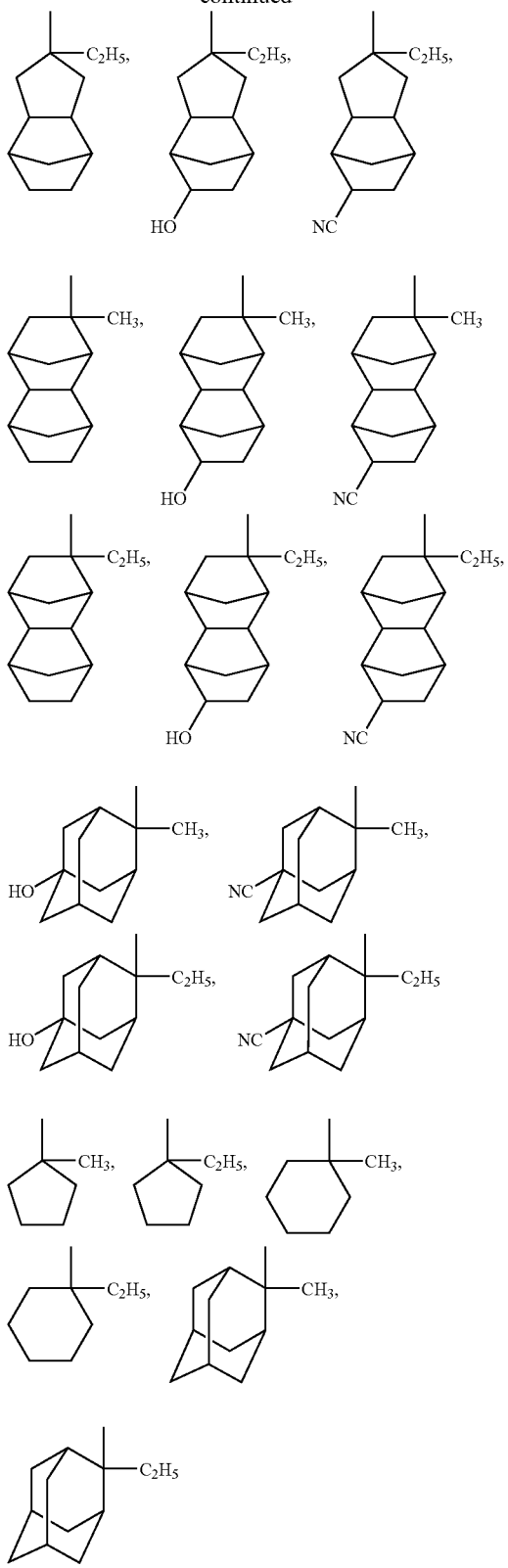

As examples of the other repeating units, repeating units derived from the monomer shown by the following formula (14) (hereinafter referred to from time to time as "other repeating unit (14)") are also preferable.

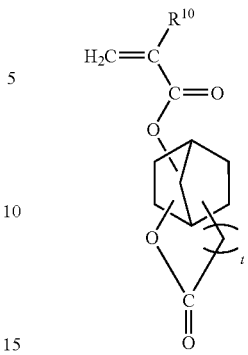

(14)

wherein $R^{10}$ represents a hydrogen atom, a methyl group, or a trifluoromethyl group, and t is 0 or 1.

Examples of the repeating units other than the other repeating units (13) and the other repeating units (14) include repeating units derived from the following monomers: monofunctional compounds such as (meth)acrylates having a bridged hydrocarbon skeleton such as norbornyl(meth)acrylate, iso-norbornyl(meth)acrylate, tricyclodecanyl(meth)acrylate, tetracyclodecanyl(meth)acrylate, dicyclopentenyl(meth)acrylate, adamantyl(meth)acrylate, and adamantylmethyl (meth)acrylate; carboxyl group-containing esters having a bridged hydrocarbon skeleton of unsaturated carboxylic acid such as carboxynorbornyl(meth)acrylate, carboxytricyclodecanyl(meth)acrylate, and carboxytetracyclodecanyl (meth)acrylate;

(meth)acrylates not having a bridged hydrocarbon skeleton such as methyl(meth)acrylate, ethyl(meth)acrylate, n-propyl (meth)acrylate, n-butyl(meth)acrylate, 2-methylpropyl (meth)acrylate, 1-methylpropyl(meth)acrylate, t-butyl (meth)acrylate, 2-hydroxyethyl(meth)acrylate, 2-hydroxypropy (meth)acrylate, 3-hydroxypropyl (meth)acrylate, cyclopropyl(meth)acrylate, cyclopentyl (meth)acrylate, cyclohexyl(meth)acrylate, 4-methoxycyclohexyl(meth)acrylate, 2-cyclopentyloxycarbonylethyl(meth)acrylate, 2-cyclohexyloxycarbonylethyl(meth)acrylate, and 2-(4-methoxycyclohexyl)oxycarbonylethyl(meth)acrylate;

α-hydroxymethylacrylates; unsaturated nitryl compounds; unsaturated amide compounds; nitrogen-containing vinyl compounds; unsaturated carboxylic acids (anhydrides) such as (meth)acrylic acid, crotonic acid, maleic acid, maleic anhydride, fumaric acid, itaconic acid, anhydrous itaconic acid, citraconic acid, anhydrous citraconic acid, and mesaconic acid; carboxyl group-containing esters not having a bridged hydrocarbon skeleton of an unsaturated carboxylic acid such as 2-carboxyethyl(meth)acrylate, 2-carboxypropyl (meth)acrylate, 3-carboxypropyl(meth)acrylate, 4-carboxybutyl(meth)acrylate, and 4-carboxycyclohexyl (meth)acrylate; (meth)acryloyloxy lactone compounds having an acid-dissociable group; and (meth)acryloyloxy lactone compounds not having an acid-dissociable group; as well as polyfunctional compounds having a bridged hydrocarbon skeleton such as 1,2-adamantanediol di(meth)acrylate, 1,3-adamantanediol di(meth)acrylate, 1,4-adamantanediol di(meth)acrylate, and tricyclodecanyl dimethylol di(meth)acrylate; and polyfunctional compounds not having a bridged hydrocarbon skeleton. Among the above monomers, (meth)acrylates having a bridged hydrocarbon skeleton are preferable.

When the resin of the present invention contains the repeating unit shown by the formula (10), the other repeating units (13), and the other repeating units (14), the content of the repeating unit shown by the formula (10) is preferably not more than 30 mol %, more preferably 1 to 30 mol %, and particularly preferably 1 to 15 mol % of all repeating units in the resin. If the content of the repeating unit shown by the formula (10) is more than 30 mol %, transparency to radiation is reduced, which may make it difficult to obtain a rectangular resist pattern. If the content is less than 1 mol %, the sensitivity and resolution may be impaired.

The content of the other repeating units (13) is preferably 10 to 80 mol %, more preferably 15 to 75 mol %, and particularly preferably 20 to 70 mol % of all the repeating units in the resin. If the content of the other repeating units (13) is less than 10 mol %, solubility of the radiation-sensitive resin composition in an alkaline developer decreases, which may cause developing defect and lower resolution. If the content exceeds 80 mol %, resolution may be impaired.

The content of the other repeating units (14) is preferably 10 to 90 mol %, more preferably 20 to 80 mol %, and particularly preferably 30 to 70 mol % of all the repeating units in the resin. If the amount of the other repeating units (14) is less than 10 mol %, adhesion with a substrate may be impaired. If the content exceeds 90 mol %, resolution may be impaired. In the above description, the total of the repeating unit shown by the formula (10), the other repeating units (13), and the other repeating units (14) is 100 mol %.

The resin of the present invention can be produced by polymerizing the monomers for forming the repeating unit shown by the formula (10), that is, the polymerizable onium sulfonate of the present invention and, as required, monomers for forming the other repeating units (for example, the other repeating units shown by the formula (13) and the other repeating units shown by the formula (14)) using a radical polymerization initiator such as a hydroperoxide, a dialkyl peroxide, a diacyl peroxide, and an azo compound and, as required, a chain transfer agent, in a suitable solvent.

Examples of the solvent used in the polymerization include alkanes such as n-pentane, n-hexane, n-heptane, n-octane, n-nonane, and n-decane; cycloalkanes such as cyclohexane, cycloheptane, cyclooctane, decalin, and norbornane; aromatic hydrocarbons such as benzene, toluene, xylene, ethylbenzene, and cumene; halogenated hydrocarbons such as chlorobutanes, bromohexanes, dichloroethanes, hexamethylene dibromide, and chlorobenzene; saturated carboxylic acid esters such as ethyl acetate, n-butyl acetate, i-butyl acetate, and methyl propionate; ketones such as 2-butanone, 4-methyl-2-pentanone, and 2-heptanone; and ethers such as tetrahydrofuran, dimethoxyethanes, and diethoxyethanes. The solvents may be used either individually or in combination of two or more. The polymerization reaction temperature is preferably 40 to 120° C., and more preferably 50 to 90° C. The reaction time is preferably 1 to 48 hours, and more preferably 1 to 24 hours.

The weight average molecular weight (Mw) measured by gel permeation chromatography of the resin of the present invention is preferably 1000 to 100,000, more preferably 1500 to 80,000, and particularly preferably 2000 to 50,000. If the Mw of the resin is less than 1000, the heat resistance of the resist may be poor. On the other hand, if more than 100,000, the resolution of the resist may be impaired. The ratio (Mw/Mn) of the Mw to the number average molecular weight (Mn) is preferably 1 to 5, and more preferably 1 to 3.

The smaller the amount of impurities such as halogens and metals in the polymer solution obtained by the polymerization, the better the resist performance such as sensitivity, resolution, process stability, and pattern form. Examples of purification method of the resin include, for example, a chemical purification method such as washing with water or liquid-liquid extraction or a combination of the chemical purification method and a physical purification method such as ultrafiltration or centrifugation. The above resins may be used either individually or in combination of two or more.

EXAMPLES

The present invention is described in detail below by way of examples. Note that the present invention is not limited to the following examples. "Part(s)" and "%" in the examples, comparative examples, and reference examples are expressed on a mass basis, unless other wise indicated.

Example 1

[Synthesis of Polymerizable Onium Sulfonate]

First, the method of producing sodium 1,1,2,2-tetrafluoro-4-hydroxybutane-1-sulfinate (first step) is described.

A 2 litter reactor was charged with 151 g (0.67 mol) of 4-bromo-3,3,4,4-tetrafluorobutan-1-ol, 600 ml of acetonitrile, 600 ml of water, 112 g (1.33 mol/2.0 equivalent)) of sodium hydrogencarbonate, and 235 g (1.35 mol/2.0 equivalent) of sodium dithionite in a nitrogen stream. The mixture was stirred at room temperature for 12 hours. The reaction solution was extracted four times with 500 ml of acetonitrile. The solvent was evaporated from the resulting organic layer to obtain 120 g of the target sodium 1,1,2,2-tetrafluoro-4-hydroxybutane-1-sulfinate. The purity of the product was 80% and the yield was 77%.

The results of $^1$H-NMR and $^{19}$F-NMR analysis of the resulting sodium 1,1,2,2-tetrafluoro-4-hydroxybutane-1-sulfinate are shown below.

$^1$H-NMR (DMSO-$d_6$): 4.69 (t, J=5.6 Hz, 1H; OH), 3.60 (q, J=6.7 Hz, 2H; $CH_2$), 2.36 (m, 2H; $CH_2$)

$^{19}$F-NMR (DMSO-$d_6$): −110.18 (m, 2F; $CF_2$), −130.54 (m, 2F; $CF_2$)

Next, the method of producing sodium 1,1,2,2-tetrafluoro-4-hydroxybutane-1-sulfonate (second step) is described.

A 1 litter reactor was charged with 120 g (0.52 mol) of sodium 1,1,2,2-tetrafluoro-4-hydroxybutane-1-sulfinate obtained above, 650 ml of water, 74 g (0.65 mol/1.26 equivalent)) of 30% hydrogen peroxide water, and 0.171 g (0.00058 mol/0.0011 equivalent) of disodium tungstate. The mixture was stirred at room temperature for one hour. Volatile components were removed from the reaction solution by heating under reduced pressure and the residue was dried to solidify to obtain 113 g of the target sodium 1,1,2,2-tetrafluoro-4-hydroxybutane-1-sulfonate. The purity of the product was 78% and the yield was 88%.

The results of $^1$H-NMR and $^{19}$F-NMR analysis of the resulting sodium 1,1,2,2-tetrafluoro-4-hydroxybutane-1-sulfonate are shown below.

$^1$H-NMR (DMSO-$d_6$): 4.69 (t, J=5.6 Hz, 1H; OH), 3.60 (q, J=6.7 Hz, 2H; $CH_2$), 2.36 (m, 2H; $CH_2$)

$^{19}$F-NMR (DMSO-$d_6$): −110.93 (m, 2F; $CF_2$), −117.93 (m, 2F; $CF_2$)

Next, the method of producing triphenylsulfonium-1,1,2,2-tetrafluoro-4-hydroxybutane-1-sulfonate (third step) is described.

Using a 2 litter reactor, 121 g of sodium 1,1,2,2-tetrafluoro-4-hydroxybutane-1-sulfonate (purity 78%, 0.38 mol) obtained in the second step was suspended in 560 g of dichloromethane. An aqueous solution of triphenylsulfonium chloride (115 g of triphenylsulfonium chloride (0.385 mol/1.01 equivalent)) and 450 g of water) was added dropwise to the suspension at room temperature. The resulting reaction solution separated in two layers was vigorously stirred at room temperature for 90 minutes to separate the organic layer. The organic layer was washed four times with 250 ml of water. Volatile components were removed from the organic layer by distillation and the residue was dried to solidify to obtain 167 g of the target triphenylsulfonium-1,1,2,2-tetrafluoro-4-hydroxybutane-1-sulfonate. The purity of the product was 97% and the yield was 93%.

The results of $^1$H-NMR and $^{19}$F-NMR analysis of the resulting triphenylsulfonium-1,1,2,2-tetrafluoro-4-hydroxybutane-1-sulfonate are shown below.

$^1$H-NMR (DMSO-d$_6$): 7.9-7.7 (15H; Ph$_3$S$^+$), 4.71 (t, J=5.6 Hz, 1H; OH), 3.62 (q, J=6.7 Hz, 2H; CH$_2$), 2.40 (m, 2H; CH$_2$)

$^{19}$F-NMR (DMSO-d$_6$): −110.93 (m, 2F; CF$_2$), −117.93 (m, 2F; CF$_2$)

Next, the method of producing triphenylsulfonium-1,1,2,2-tetrafluoro-4-(2-methylacryloyloxy)-butane-1-sulfonate (fourth step) is described.

A 2 litter reactor was charged with 451 g (0.92 mol) of the triphenylsulfonium-1,1,2,2-tetrafluoro-4-hydroxybutane-1-sulfonate obtained in the third step, 1.92 kg of chloroform, 177 g (1.15 mol/1.24 equivalent) of methacrylic acid anhydride, 53.7 g (0.00056 mol/0.00061 equivalent) of methanesulfonic acid, and 0.65 g of Nonflex MBP (2,2'-methylenebis (4-methyl-6-tert-butylphenol) manufactured by Seiko Chemical Co., Ltd.). The mixture was stirred at 45° C. for six hours. After cooling, the reaction mixture was washed seven times with 1.5 kg of water and heated under reduced pressure to evaporate volatile components from the organic layer. The resulting liquid was washed three times with 250 g of diisopropyl ether and dried to obtain 478 g of the target triphenylsulfonium-1,1,2,2-tetrafluoro-4-(2-methylacryloyloxy)-butane-1-sulfonate (the compound shown by the formula (1-1). The purity of the product was 97% and the yield was 93%.

The results of $^1$H-NMR and $^{19}$F-NMR analysis of the resulting triphenylsulfonium-1,1,2,2-tetrafluoro-4-(2-methylacryloyloxy)-butane-1-sulfonate are shown below.

$^1$H-NMR (CDCl$_3$): 7.8-7.6 (15H; Ph$_3$S$^+$), 6.04 (s, 1H; C═CH$_2$), 5.49 (m, 1H; C═CH$_2$), 4.35 (t, J=6.7 Hz, 2H; O—CH$_2$), 2.72 (m, 2H; CH$_2$), 1.85 (s, 3H; CH$_3$)

$^{19}$F-NMR (CDCl$_3$): −112.88 (m, 2F; CF$_2$), −118.71 (m, 2F; CF$_2$)

The triphenylsulfonium-1,1,2,2-tetrafluoro-4-(2-methylacryloyloxy)-butane-1-sulfonate product obtained in this manner is designated as compound (I).

Comparative Example 1

A 100 ml reactor was charged with 5 g (0.0215 mol) of the sodium 1,1,2,2-tetrafluoro-4-hydroxybutane-1-sulfinate obtained in the same manner as in the first step of Example 1, 25 g of chloroform, 4.1 g (0.0266 mol/1.24 equivalent) of methacrylic acid anhydride, 15 mg (0.00016 mol/0.0074 equivalent) of methanesulfonic acid, and 10 mg of Nonflex MBP (2,2'-methylenebis(4-methyl-6-tert-butylphenol) manufactured by Seiko Chemical Co., Ltd.).

As a result, it was found that the sodium 1,1,2,2-tetrafluoro-4-hydroxybutane-1-sulfinate was not dissolved. After the addition of the above components, the mixture was stirred at 50° C. for 12 hours to find that the reaction did not proceed.

Comparative Example 2

A 100 ml reactor was charged with 5 g (0.0215 mol) of sodium 1,1,2,2-tetrafluoro-4-hydroxybutane-1-sulfinate obtained in the same manner as in the first step of Example 1, 25 g of acetonitrile, 4.1 g (0.0266 mol/1.24 equivalent) of methacrylic acid anhydride, 15 mg (0.00016 mol/0.0074 equivalent) of methanesulfonic acid, and 10 mg of Nonflex MBP (2,2'-methylenebis(4-methyl-6-tert-butylphenol) manufactured by Seiko Chemical Co., Ltd.).

Although the sodium 1,1,2,2-tetrafluoro-4-hydroxybutane-1-sulfinate was dissolved, the reaction did not proceed after stirring the mixture at 50° C. for six hours.

Comparative Example 3

A 100 ml reactor was charged with 5 g (0.02 mol) of the sodium 1,1,2,2-tetrafluoro-4-hydroxybutane-1-sulfonate obtained in the same manner as in the first and second steps of Example 1, 25 g of chloroform, 4 g (0.0259 mol/1.30 equivalent) of methacrylic acid anhydride, 15 mg (0.00016 mol/0.008 equivalent) of methanesulfonic acid, and 10 mg of Nonflex MBP (2,2'-methylenebis(4-methyl-6-tert-butylphenol) manufactured by Seiko Chemical Co., Ltd.).

As a result, it was found that the sodium 1,1,2,2-tetrafluoro-4-hydroxybutane-1-sulfonate was not dissolved. After the addition of the above components, the mixture was stirred at 50° C. for 12 hours to find that the reaction did not proceed.

Comparative Example 4

A 100 ml reactor was charged with 5 g (0.02 mol) of sodium 1,1,2,2-tetrafluoro-4-hydroxybutane-1-sulfonate obtained in the same manner as in the first and second steps of Example 1, 25 g of acetonitrile, 4 g (0.0259 mol/1.30 equivalent) of methacrylic acid anhydride, 15 mg (0.00016 mol/0.008 equivalent) of methanesulfonic acid, and 10 mg of Nonflex MBP (2,2'-methylenebis(4-methyl-6-tert-butylphenol) manufactured by Seiko Chemical Co., Ltd.).

As a result, it was found that the sodium 1,1,2,2-tetrafluoro-4-hydroxybutane-1-sulfonate was not dissolved. After the addition of the above components, the mixture was stirred at 50° C. for eight hours to find that the reaction did not proceed.

Comparative Example 5

In this Comparative Example, the reactions were carried out in the order of the first step, the third step, the fourth step, and the second step. Specifically, the reactions were carried out as follows. The reaction of the first step was carried out in the same manner as in Example 1 to obtain the sodium 1,1,2,2-tetrafluoro-4-hydroxybutane-1-sulfinate. Next, the reaction of the third step was carried out using a 100 ml reactor, in which 6 g of the sodium 1,1,2,2-tetrafluoro-4-hydroxybutane-1-sulfinate (purity 80%, 0.0207 mol) obtained above was suspended in 30 g of dichloromethane. An aqueous solution of triphenylsulfonium chloride (6.3 g (0.0211 mol/1.02 equivalent) of triphenylsulfonium chloride and 25 g of water) was added dropwise to the suspension at room temperature. The resulting reaction solution separated in two layers was vigorously stirred at room temperature for one hour to separate the organic layer. The organic layer was washed four times with 20 ml of water. Volatile components were removed from the organic layer by distillation and the residue was dried to solidify to obtain 10 g of the target triphenylsulfonium-1,1,2,2-tetrafluoro-4-hydroxybutane-1-sulfinate. The purity of the product was 80% and the yield was 82%.

Next, the reaction of the fourth step was carried out using a 100 ml reactor, which was charged with 10 g (0.017 mol) of the above triphenylsulfonium-1,1,2,2-tetrafluoro-4-hydroxybutane-1-sulfinate (purity 80%), 50 g of chloroform, 3.25 g 1 (0.021 mol/1.24 equivalent) of methacrylic acid anhydride, 15 mg (0.00016 mol/0.0094 equivalent) of methanesulfonic acid, and 10 mg of Nonflex MBP (2,2'-methylenebis(4-methyl-6-tert-butylphenol) manufactured by Seiko Chemical Co., Ltd.). The mixture was stirred for 12 hours while heating at 50° C. After that, the reaction mixture was cooled, washed five times with 50 g of water, and distilled under reduced pressure to evaporate volatile components from the organic layer. The liquid thus obtained was washed three times with 40 g of diisopropyl ether and dried to obtain 7.2 g of the target triphenylsulfonium-1,1,2,2-tetrafluoro-4-(2-methylacryloyloxy)-butane-1-sulfinate. The purity of the compound was 95% and the yield was 78%.

Next, the second step reaction was carried out using a 100 ml reactor, which was charged with 5 g (0.00925 mol) of 1,1,2,2-tetrafluoro-4-(2-methylacryloyloxy)-butane-1-sulfinate, 27 ml of water, 1.36 g (0.012 mol/1.26 equivalent)) of 30% hydrogen peroxide water, and 3 mg (0.00001 mol/0.0011 equivalent) of disodium tungstate. The mixture was stirred at room temperature for one hour.

As a result, the target triphenylsulfonium-1,1,2,2-tetrafluoro-4-(2-methylacryloyloxy)-butane-1-sulfonate product was not obtained at all.

The molecular weight (Mw, Mn) and Mw/Mn in the Examples and Comparative Examples were carried out according to the following procedures.

[Method of Measuring Molecular Weight (Mw and Mn)]

A detector MALLS was used for the molecular weight (Mw, Mn) measurement of the resins. Molecular weight was measured by gel permeation chromatography (GPC) using GPC columns (TSKgel α-2500 and TSKgel α-M, manufactured by Tosoh Corp.) under the following conditions: flow rate: 1.0 ml/min., eluate: solution of LiBr (30 mmol/l)/$H_3PO_4$ (10 mmol/l) in dimethyl formamide, column temperature: 40° C., detector: MALLS (DAWN DSP manufactured by Wyatt, cell type K5, laser wavelength: 632.8 nm)

Example 2

Synthesis of Resin

In 60 g of 2-butanone, 10.98 g (52 mol %) of the following compound (M-1), 7.96 g (46 mol %) of the following compound (M-2), 1.06 g (2 mol %) of the compound (1) obtained in Example 1 were dissolved. On the other hand, a monomer solution was prepared by adding 0.78 g of 2,2'-azobisisobutyronitrile (AIBN). A 100 ml three-neck flask charged with 20 g of 2-butanone was purged with nitrogen for 30 minutes. After the nitrogen purge, the reaction vessel was heated to 80° C. while stirring and the previously prepared monomer solution was added dropwise using a dropping funnel over three hours. Assuming that the polymerization was started at the time of initiating the dropwise addition of the monomer solution, the polymerization reaction was carried out for six hours. After the polymerization, the polymer solution was cooled with water to 30° C. or less and added to 100 g of 2-propanol. A deposited white powder was collected by filtration.

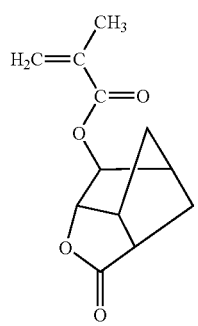

(M-1)

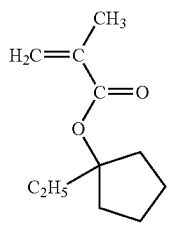

(M-2)

The collected white powder in the form of a slurry was washed twice with 500 g of 2-propanol, followed by further filtration and drying at 50° C. for 17 hours to obtain a white powdery polymer (10 g, yield: 68%). The polymer was a copolymer with Mw of 11,900 and Mw/Mn=1.27 (result of MALLS analysis). As a result of $^{13}$C-NMR analysis, the ratio of the repeating unit derived from the compound (M-1), the repeating unit derived from the compound (M-2), and the repeating unit derived from the compound (I) was 64.3:33.5:2.2 (mol %). The copolymer is referred to as a resin (A-1).

Example 3

A resin (A-2) was prepared in the same manner as in Example 2, except for changing the amount of the monomers and the initiator as shown in Table 1. The resin (A-2) was a copolymer with Mw=12,800 and Mw/Mn=1.19 (result of MALLS analysis) and the ratio of the repeating unit derived from the compound (M-1), the repeating unit derived from the compound (M-2), and the repeating unit derived from the compound (I) was 60.9:35.0:4.1.

TABLE 1

| | Monomer | | | | | |
|---|---|---|---|---|---|---|
| | Type | Amount (mol %) | Type | Amount (mol %) | Type | Amount (mol %) |
| Example 2 | M-1 | 52 | M-2 | 46 | Compound (1) | 2 |
| Example 3 | M-1 | 50 | M-2 | 46 | Compound (1) | 4 |
| Comparative Example 6 | M-1 | 50 | M-2 | 50 | — | — |

Comparative Example 6

A resin (R-1) was prepared in the same manner as in Example 2, except for changing the amount of the monomers and the initiator as shown in Table 1. The resin (R-1) was a copolymer with Mw=11,600 and Mw/Mn=1.21 (result of MALLS analysis) and the ratio of the repeating unit derived from the compound (M-1), the repeating unit derived from the compound (M-2), and the repeating unit derived from the compound (1) was 60.5:39.5:0.

Reference Example 1

Preparation of Radiation-Sensitive Resin Composition Solution

A radiation-sensitive resin composition solution was prepared by mixing and homogenizing 50 parts of the resin (A-1), 50 parts of the resin (A-2), 1.10 part of N-t-butoxycarbonyl-4-hydroxypiperidine (indicated as (D-1) in Table 2) as an acid diffusion controller, 1400 parts of propylene glycol monomethyl ether acetate (indicated as (C-1) in Table 2) as a solvent, and 600 parts of cyclohexanone (indicated as (C-2) in Table 2) as a solvent, and filtering the solution through a membrane filter with a pore diameter of 200 nm. The resulting radiation-sensitive resin composition solution was evaluated as follows.

[Sensitivity]

The radiation-sensitive resin composition solutions prepared in Reference Examples and Comparative Reference Example were applied by spin-coating to substrates which were prepared by forming ARC29A (manufactured by Nissan Chemical Co., Ltd.) film with a thickness of 77 nm on a wafer surface. The coating was prebaked (PB) on a hot plate at 100° C. for 90 seconds to obtain a resist film with a thickness of 200 nm. The resist film was exposed to radiation through a mask pattern using a full field reduced projection exposure apparatus, "S306C" (numerical aperture 0.75) manufactured by NIKON Corp. After PEB at 110° C. for 90 seconds, the resist was developed using a 2.38 mass % aqueous solution of TMAH at 25° C. for 60 seconds, washed with water, and dried to obtain a positive-tone resist pattern. In this instance, an optimal exposure amount required for forming a 1:1 line-and-space pattern (with a line width of 100 nm via a mask pattern with a 100 nm 1:1 line-and-space pattern was regarded as an optimal exposure dose (J/cm$^2$), which was taken as the sensitivity.

[Resolution]

The minimum dimension (μm) of the 1:1 line-and-space pattern resolved at the optimum exposure dose in the above evaluation of sensitivity was taken as the resolution.

[LER]

The line width on the 100 nm 1:1 line-and-space pattern developed by the optimum exposure dose in the above evaluation of sensitivity was inspected from above the pattern using "SEM S9220" manufactured by Hitachi, Ltd. at arbitrary points to evaluate line width fluctuation by the three sigma method. The lower the value (nm) of LER, the better the roughness.

[DOF]

The resist film was exposed to radiation at the optimum dose in the sensitivity evaluation by off-setting the depth of focuses at intervals of 0.05 μm from −1.0 μm to +1.0 μm. The range (μm) in which the line width increases from 90 nm (−10%) to 110 nm (+10%) was regarded as DOF. The larger the value of DOF, the better the depth of focus allowance.

In this Reference Example, the evaluation results of sensitivity were as follows: sensitivity: 440 J/m$^2$, resolution: 0.09 μm, DOF: 0.8 μm, and LER: 3.8 μm.

Reference Example 2 and Comparative Reference Example 1

Radiation-sensitive resin composition solutions were prepared in the same manner as in Reference Example 1, except for using the components of the formulations shown in Table 2. The results of the evaluation are shown in Table 3.

TABLE 2

| | Resin | | | | Other acid generator | | Acid diffusion controller | | Solvent | | | |
|---|---|---|---|---|---|---|---|---|---|---|---|---|
| | Type | Amount (part) | Type | Amount (part) | Type | Amount (part) | Type | Amount (part) | Type | Amount (part) | Type | Amount (part) |
| Reference Example 1 | A-1 | 50 | A-2 | 50 | — | — | D-1 | 1.10 | C-1 | 1400 | C-2 | 600 |
| Reference Example 2 | A-1 | 50 | A-2 | 50 | B-1 | 1.0 | D-1 | 1.40 | C-1 | 1400 | C-2 | 600 |
| Comparative Reference Example 1 | R-1 | 100 | — | — | B-1 | 4.0 | D-1 | 0.80 | C-1 | 1400 | C-2 | 600 |

TABLE 3

| | Sensitivity (J/m$^2$) | Resolution (μm) | DOF (μm) | LER (μm) |
|---|---|---|---|---|
| Reference Example 1 | 440 | 0.09 | 0.8 | 3.8 |
| Reference Example 2 | 450 | 0.09 | 0.7 | 3.7 |
| Comparative Reference Example 1 | 460 | 0.10 | 0.6 | 6.5 |

In Table 2, "B-1" indicates triphenylsulfonium nonafluoro-n-butane sulfonate, "B-2" indicates triphenylsulfonium trifluoromethane sulfonate, and "D-2" indicates 3-piperidino (piperidino)-1,2-propanediol.

As clear from Table 3, the radiation-sensitive resin compositions of Reference Examples 1 and 2 which contain the resins of the present invention (resins of Examples 2 and 3) were confirmed to exhibit good evaluation results as compared with the radiation-sensitive resin composition of Comparative Reference Example 1 which contains the resin of Comparative Example 6.

Specifically, the radiation-sensitive resin composition containing the resin of the present invention can form a chemically-amplified resist responsive to deep ultraviolet rays represented by activated rays such as a KrF excimer laser (wavelength: 248 nm) and an ArF excimer laser (wavelength: 193 nm). The chemically-amplified resist exhibits high resolution and particularly wide DOF, and is excellent in LER. Thus, the resist can be suitably used in the manufacture of integrated circuit devices which are expected to be further miniaturized in the future.

INDUSTRIAL APPLICABILITY

This resin can be very suitably used as a radiation sensitive acid generator in positive-tone and negative-tone radiation-sensitive resin compositions which are useful particularly as chemically-amplified resists.

The invention claimed is:

1. A polymerizable onium sulfonate shown by the following formula (1),

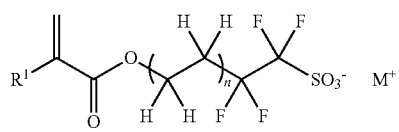
(1)

wherein $R^1$ represents a hydrogen atom, a fluorine atom, or an alkyl group having 1 to 3 carbon atoms, in which some or all of the hydrogen atoms may be substituted by a fluorine atom, $M^+$ represents a sulfonium cation shown by the following formula (2) or an iodonium cation shown by the following formula (3), and n represents 1,

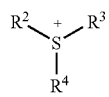
(2)

wherein $R^2$, $R^3$, and $R^4$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or two or more of $R^2$, $R^3$, and $R^4$ may bond to form a ring together with the sulfur atom in the formula (2),

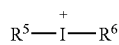
(3)

wherein $R^5$ and $R^6$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 carbon atoms, or $R^5$ and $R^6$ may bond to form a ring together with the iodine atom in the formula (3).

2. The polymerizable onium sulfonate according to claim 1, the polymerizable onium sulfonate being a compound shown by the following formula (1-1),

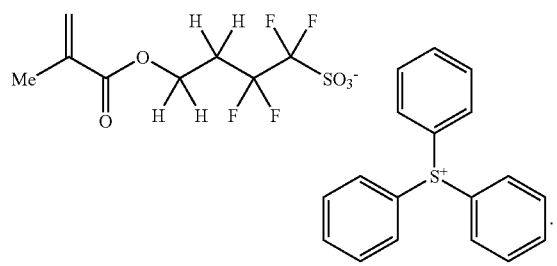
(1-1)

3. A process for producing a polymerizable onium sulfonate comprising a first step of sulfinating 4-bromo-3,3,4,4-tetrafluorobutan-1-ol using a sulfinating agent to obtain a metal sulfinate shown by the following formula (4), a second step of oxidizing the metal sulfinate using an oxidizer to obtain a metal sulfonate shown by the following formula (5), a third step of reacting the metal sulfonate with a monovalent onium salt shown by the following formula (6) to obtain an onium sulfonate shown by the following formula (7), and a fourth step of reacting the onium sulfonate with an alkyl acrylic acid halide shown by the following formula (8) or an alkyl acrylic acid anhydride shown by the following formula (9) to obtain a polymerizable onium sulfonate shown by the following formula (1-a),

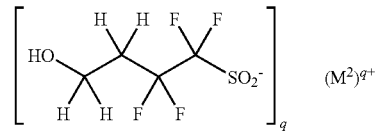
(4)

wherein $(M^2)^{q+}$ shows a counter cation that is a metal ion and q is an arbitrary integer,

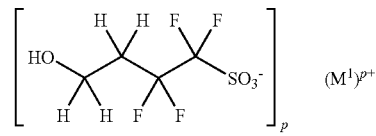
(5)

wherein $(M^1)^{p+}$ shows a counter cation that is a metal ion and p is an arbitrary integer, $$M^+X^-$$ (6)

wherein $M^+$ shows a sulfonium cation shown by the following formula (2) or an iodonium cation shown by the following formula (3) and $X^-$ shows a monovalent anion,

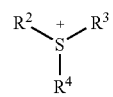
(2)

wherein $R^2$, $R^3$, and $R^4$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or two or more of $R^2$, $R^3$, and $R^4$ may bond to form a ring together with the sulfur atom in the formula (2), (3)

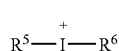

wherein $R^5$ and $R^6$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 carbon atoms, or $R^5$ and $R^6$ may bond to form a ring together with the iodine atom in the formula (3), (7)

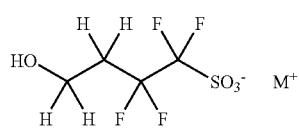

wherein $M^+$ is the same as $M^+$ in the formula (6), (8)

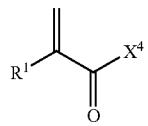

wherein $R^1$ represents a hydrogen atom, a fluorine atom, or an alkyl group having 1 to 3 carbon atoms, in which some or all of the hydrogen atoms may be substituted by a fluorine atom, $X^4$ represents a fluorine atom, a chlorine atom, a bromine atom, or an iodine atom, (9)

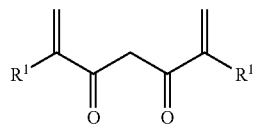

wherein $R^1$ is the same as the $R^1$ in the formula (8), (1-a)

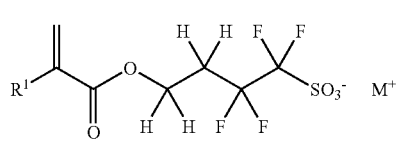

wherein $R^1$ is the same as the $R^1$ in the formula (8) and $M^+$ is the same as the $M^+$ in the formula (6).

4. A resin comprising a repeating unit shown by the following formula (10), (10)

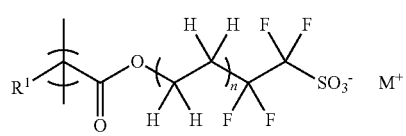

wherein $R^1$ represents a hydrogen atom, a fluorine atom, or an alkyl group having 1 to 3 carbon atoms, in which some or all of the hydrogen atoms may be substituted by a fluorine atom, $M^+$ represents a sulfonium cation shown by the following formula (2) or an iodonium cation shown by the following formula (3), and n represents 1, (2)

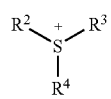

wherein $R^2$, $R^3$, and $R^4$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 atoms, or two or more of $R^2$, $R^3$, and $R^4$ may bond to form a ring together with the sulfur atom in the formula (2), (3)

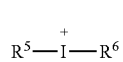

wherein $R^5$ and $R^6$ individually represent a substituted or unsubstituted linear or branched alkyl group having 1 to 30 carbon atoms, a substituted or unsubstituted cyclic monovalent hydrocarbon group having 3 to 30 carbon atoms, a substituted or unsubstituted aryl group having 6 to 30 carbon atoms, or an unsubstituted monovalent heterocyclic organic group having 4 to 30 carbon atoms, or $R^5$ and $R^6$ may bond to form a ring together with the iodine atom in the formula (3).

* * * * *